United States Patent
Acemoglu et al.

(10) Patent No.: US 7,906,677 B2
(45) Date of Patent: Mar. 15, 2011

(54) PROCESS FOR PHENYLACETIC ACID DERIVATIVES

(75) Inventors: Murat Acemoglu, Basel (CH); Thomas Allmendinger, Lörrach (DE); John Vincent Calienni, Cranford, NJ (US); Jacques Cercus, Rixheim (FR); Olivier Loiseleur, Saint-Louis (FR); Gottfried Sedelmeier, Schallstadt (DE); David Xu, Whippany, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/436,991

(22) Filed: May 7, 2009

(65) Prior Publication Data
US 2009/0275758 A1 Nov. 5, 2009

Related U.S. Application Data

(63) Continuation of application No. 11/893,481, filed on Aug. 16, 2007, now abandoned, which is a continuation of application No. 10/089,038, filed on Mar. 25, 2002, now abandoned.

(30) Foreign Application Priority Data

Sep. 27, 1999 (GB) .................................. 9922830.6

(51) Int. Cl.
C07C 227/22 (2006.01)
C07C 209/62 (2006.01)
(52) U.S. Cl. ........................................ 562/456; 564/413
(58) Field of Classification Search .................. 548/486; 562/456; 564/305, 413, 202, 211
See application file for complete search history.

(56) References Cited

U.S. PATENT DOCUMENTS

| | | | |
|---|---|---|---|
| 3,558,690 A | 1/1971 | Sallmann et al. |
| 4,602,932 A | 7/1986 | Handte et al. |
| 4,668,276 A | 5/1987 | Handte et al. |
| 4,978,773 A | 12/1990 | Grafe et al. |
| 5,475,139 A | 12/1995 | Lee et al. |
| 5,576,460 A | 11/1996 | Buckwald et al. |
| 5,585,357 A | 12/1996 | Dolle et al. |
| 5,677,283 A | 10/1997 | Dolle et al. |
| 5,817,877 A | 10/1998 | Hartwig et al. |
| 5,869,667 A | 2/1999 | Bessard et al. |
| 6,034,266 A | 3/2000 | Boechat et al. |
| 6,291,523 B1 | 9/2001 | Fujimoto et al. |
| 6,552,077 B2 | 4/2003 | Cohen |

FOREIGN PATENT DOCUMENTS

| | | |
|---|---|---|
| EP | 0152006 | 1/1985 |
| EP | 0154153 | 1/1985 |
| EP | 196260 | 10/1986 |
| EP | 0644198 | 6/1994 |
| EP | 0380712 | 1/1995 |
| EP | 0819679 | 1/1998 |
| GB | 2023578 A | 1/1980 |
| JP | A-56-77246 | 6/1981 |
| JP | 2215750 | 8/1990 |
| JP | 9-323962 | 12/1997 |
| WO | WO92/22522 | 12/1992 |
| WO | WO95/29672 | 11/1995 |
| WO | 99/11605 | 3/1999 |

OTHER PUBLICATIONS

Wolff et al., Burger's Medicinal Chemistry and Drug Discovery, Wiley-Interscience, Fifth Edition, vol. 1, Principles and Practice, pp. 975-977, (1994).

(Continued)

*Primary Examiner* — Kamal A Saeed
*Assistant Examiner* — Kristin Bianchi
(74) *Attorney, Agent, or Firm* — Leslie Fischer; Jennifer C. Chapman

(57) ABSTRACT

A process for the production of a compound of Formula I, or a pharmaceutically acceptable salt thereof, or a pharmaceutically acceptable prodrug ester thereof,

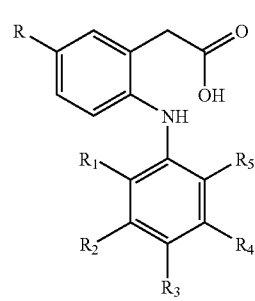

comprising cleaving a lactam of formula II

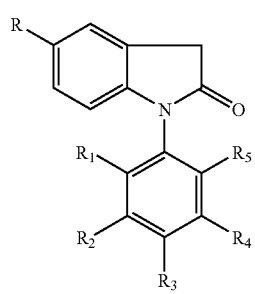

wherein the symbols are as defined, with a base; and precursors therefor and processes for the preparation of the precursors. The compounds of Formula I are pharmaceutically active compounds which are selective inhibitors of Cyclooxygenase II.

5 Claims, No Drawings

OTHER PUBLICATIONS

Bansal, O. et al.; Synthesis and pharmacology of some new 3, 4-diaryl-5-aryloxymenthyl-1,2,4-triazoles:, Indian Journal of Chemistry, vol. 31B, pp. 289-292, Apr. 1992.

Hartwig, J. et al., "Palladium-Catalysed Amination...", Synlette, pp. 329-340, Apr. 18, 1996.

Hartwig, J. et al., "Palladium-Catalysed Amination...", J. Organic Chemistry, vol. 62, pp. 1268-1273, 1997.

Wolfe, J., et al., "Nickel Cataylsed Amination of Aryl Chlorides" J. Organic Chemistry, vol. 119, pp. 6054-6058, 1997.

Wolfe, J., et al, "An Ammonia Equivalent for the Palladium-Catalyzed Amination of Aryl Halides and Triflates", Elsevier Science Ltd., Tetrahedron Letters, vol. 38, No. 36, pp. 6367-6370, 1997.

Wolfe, J., et al, "An Improved Catalyst System...", Communications to the Editor, J. American Chem. Society, vol. 118, pp. 7215-7216, 1996.

Frost, C., et al., "Iterative Animation Strategy in the Synthesis of Peptidomimetics", Sch. of Chem, Univ. Bath, Chemistry Letters, pp. 1159-1160, 1997.

Mac Neil et al, "Directed Ortho and Remote Metalation...", Synlett, pp. 419-421, Apr. 1998.

Hori, K.. et. al, "Synthesis of Nonsubstituted Anilines...", J. American Chem. Soc., vol. 120, pp. 7651-7652, Apr. 1998.

Hartwig, J. et al.,"Sterically Hindered Chelating Alkyl Phosphines...", J. American Chem. Soc. vol. 120, pp. 7369-7370, 1998.

Hartwig, J. et al, "Sterically Hindered Chelating Alkyl Phosphines...", Additions and Corrections, J. American Chem. Soc. vol. 120, No. 48, pp. 12706, 1998.

Sadighi et al, "A Highly Active Palladium Catalyst System for the Arylation of Anilines", Tetrahedon Letters, vol. 39, pp. 5327-5330, 1998.

Hartwig, J. et al, J. American Chem. Soc., vol. 120, pp. 3694-3703, 1998.

Poe, Russel et al., "Chemistry and kinetics singlet (pentafluorophenyl)nitrene", J. Am. Chem. Soc., 114(13), pp. 5064-5067, (1992).

J.F. Hartwig. "Transition metal catalyzed synthesis of arylamines and aryl ethers from aryl halides and triflates: scope and mechanism", Angewandte Chemie, International Edition, vol. 37, pp. 2046-2067, (1998).

"The Merck Index 12th Edition", Merck Research Laboratories, Whitehouse Station, NJ, p. ONR-85, Paragraph 353, (1996).

PROCESS FOR PHENYLACETIC ACID DERIVATIVES

This is a continuation of application Ser. No. 11/893,481 filed on Aug. 16, 2007, which is a continuation of application Ser. No. 10/089,038 filed on Mar. 25, 2002, which is National Stage of International Application No. PCT/EP00/09346 filed on Sep. 25, 2000, the entire disclosures of which are hereby incorporated by reference.

The present invention relates to processes for the production of 2-phenylamino-5-alkylphenyl acetic acids (the compounds of formula I given below), intermediates therefor and pharmaceutically acceptable salts thereof and pharmaceutically acceptable prodrug esters thereof;

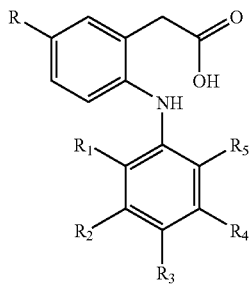

I wherein
R is methyl or ethyl;
$R_1$ is chloro or fluoro;
$R_2$ is hydrogen or fluoro;
$R_3$ is hydrogen, fluoro, chloro, methyl, ethyl, methoxy, ethoxy or hydroxy,
$R_4$ is hydrogen or fluoro; and
$R_5$ is chloro, fluoro, trifluoromethyl or methyl,
provided that $R_1$, $R_2$, $R_4$ and $R_3$ are not all fluoro when R is ethyl and $R_3$ is H.

Accordingly in a first aspect the invention provides a process for the production of a compound of Formula I, or a pharmaceutically acceptable salt thereof, or a pharmaceutically acceptable and physiologically cleavable prodrug ester thereof, comprising cleaving a lactam of formula II

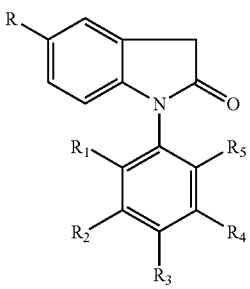

II wherein the symbols are as defined above with a base.

The above processes may include, if desired, temporarily protecting any interfering reactive groups and then isolating the resulting compound of the invention; and, if desired, converting the free carboxylic acid of the compound of formula I into a pharmaceutically acceptable ester derivative thereof; and/or if desired, converting the free acid of formula I into a salt or a resulting salt into the free acid or into another salt.

The above processes may be carried out under conditions known in the art for the hydrolytic cleavage of lactams, preferably with a strong base, such as aqueous sodium hydroxide (e.g. a 30% aqueous solution of NaOH), optionally in the presence of a water miscible organic solvent such as ethanol or methanol, preferably at elevated temperature, e.g. at a temperature in the range from about 50° to 100° C., (for instance as generally described in U.S. Pat. No. 3,558,690). The resultant reaction mixture is conveniently neutralised with an acid, e.g. a mineral acid such as hydrochloric acid to give the free acid product of formula I, which may be recovered by crystallisation, e.g. on cooling of the reaction mixture to ambient temperature, and filtration.

Pharmaceutically acceptable prodrug esters are ester derivatives which are convertible by solvolysis or under physiological conditions to the free carboxylic acids of formula I. Such esters are e.g. lower alkyl esters (such as the methyl or ethyl ester), carboxy-lower alkyl esters such as the carboxymethyl ester, nitrooxy-lower alkyl esters (such as the 4-nitrooxybutyl ester), and the like.

Pharmaceutically acceptable salts represent metal salts, such as alkaline metal salts, e.g. sodium, potassium, magnesium or calcium salts, as well as ammonium salts, which are formed e.g. with ammonia and mono- or di-alkylamines, such as diethylammonium salts, and with amino acids such as arginine and histidine salts.

Preferred compounds of formula I which may be prepared according to the present invention include:
5-methyl-2-(2",4'-dichloro-6'-methylanilino)phenylacetic acid;
5-methyl-2-(2',3',5',6'-tetrafluoroanilino)phenylacetic acid;
5-methyl-2-(2',3',4',6'-tetrafluoroanilino)phenylacetic acid;
5-methyl-2-(2',6'-dichloroanilino)phenylacetic acid;
5-methyl-2'-(2',6'-dichloroanilino)phenylacetic acid, potassium salt;
5-methyl-2-(2',6'-dichloroanilino)phenylacetic acid, sodium salt;
5-methyl-2-(2'-chloro-6'fluoroanilino)phenylacetic acid;
5-methyl-2-(2',6'-dichloro-4'-methylanilino)phenylacetic acid;
5-methyl-(2'-chloro-6'-methylanilino)phenylacetic acid;
5-methyl-2-(2',4'-difluoro-6'-chloroanilino)phenylacetic acid;
5-methyl-2-(2'-fluoro-4',6'-chloroanilino)phenylacetic acid;
5-methyl-2-(2'-chloro-4'-fluoro-6'-methylanilino)phenylacetic acid;
5-ethyl-2-(2'-fluoro-6'-chloroanilino)phenylacetic acid;
5-ethyl-2-(2'-chloro-6'-methylanilino)phenylacetic acid;
5-ethyl-2-(2',3',6'-trifluroanilino)phenylacetic acid;
5-ethyl-2-(2',3',5',6'-tetrafluoro-4'-ethoxyanilino)phenylacetic acid;
5-ethyl-2-(2'-chloro-4',6'-difluoroanilino)phenylacetic acid;
5-ethyl-2-(2',4'-dichloro-6'-fluoroanilino)phenylacetic acid;
5-ethyl-2-(2',4'-dichloro-6'-methylanilino)phenylacetic acid;
5-ethyl-2-(2'-fluoro-4'-chloro-6'-methylanilino)phenylacetic acid;
5-ethyl-2-(2',4'-difluoro-6'-methylanilino)phenylacetic acid;
5-ethyl-2-(2'-chloro-4'-fluoro-6'-methylanilino)phenylacetic acid;
5-methyl-2-(2'-chloro-4'-hydroxy-6'-fluoroanilino)phenylacetic acid;
5-methyl-2-(2'-fluoro-6'-trifluoromethylanilino)phenylacetic acid, and
5-methyl-2-(2',4'-dichloro-6'-trifluoromethylanilino)phenylacetic acid,
and pharmaceutically acceptable salts thereof; and pharmaceutically acceptable prodrug esters thereof.

Particularly preferred compounds of formula I which may be prepared according to the present invention include:

5-methyl-2-(2',3',4',6'-tetrafluoroanilino)phenylacetic acid;
5-methyl-2-(2',6'-dichloroanilino)phenylacetic acid;
5-methyl-2-(2'-chloro-6'fluoroanilino)phenylacetic acid;
5-methyl-2-(2',6'-dichloro-4'-methylanilino)phenylacetic acid;
5-methyl-2-(2'-chloro-6'-methylanilino)phenylacetic acid;
5-methyl-2-(2'-chloro-4'-fluoro-6'-methylanilino)phenylacetic acid;
5-ethyl-2-(2'-fluoro-6'-chloroanilino)phenylacetic acid;
5-ethyl-2-(2'-chloro-6'-methylanilino)phenylacetic acid;
5-ethyl-2-(2',3'6'-trifluroanilino)phenylacetic acid, and
5-ethyl-2-(2',4'-dichloro-6'-methylanilino)phenylacetic acid, and pharmaceutically acceptable salts thereof; and pharmaceutically acceptable prodrug esters thereof.

Thus, preferably also the processes of the invention may be used to prepare compounds of formula I in which R is methyl or ethyl; $R_1$, is chloro or fluoro; $R_2$ is hydrogen; $R_3$ is hydrogen, fluoro, chloro, methyl or hydroxy; $R_4$ is hydrogen; $R_5$ is chloro, fluoro or methyl; or a pharmaceutically acceptable salt or a pharmaceutically acceptable prodrug ester thereof.

The lactam of formula II may be prepared by oxidation of a lactam of formula III

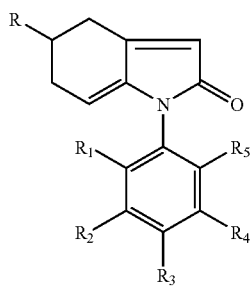

III wherein the symbols are as defined above.

Standard mild oxidation conditions may be used, such as heating with catalytical amounts of palladium on charcoal in a proper solvent, e.g. xylene.

The lactam of formula III may be prepared by coupling an aniline derivative of formula IV

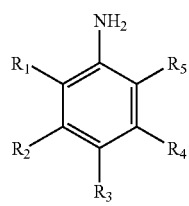

IV wherein the symbols are as defined above, with a cyclohexanone derivative of formula Va or an amino substituted cyclohexene derivative of formula Vb

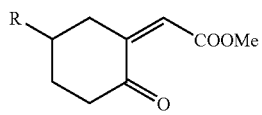

Va

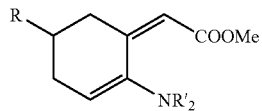

Vb wherein R is ethyl or methyl and R' is lower alkyl or similar.

Coupling of IV with Va and Vb typically involves elimination of water or the secondary amine, $HNR'_2$, e.g. under acidic conditions.

Vb may be prepared by reaction of the amino substitutes cyclohexene derivative of formula Vb'

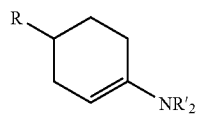

Vb' wherein R and R' are as defined above, with methyl or ethyl glyoxylate. Vb may be converted to Va by hydrolysis, for instance as hereinafter described in the Examples.

Alternatively the lactam of formula II is obtained by cyclisation of a compound of formula VII

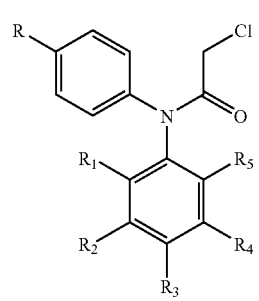

VII wherein the symbols are as defined above.

The cyclisation process is conveniently carried out under Friedel-Crafts alkylation conditions, e.g. in the presence of a Friedel-Crafts catalyst such as aluminium chloride or ethyl aluminium dichloride, preferably at elevated temperature, e.g. a temperature in the range from about 100° to about 180° C. The cyclisation reaction may be carried out in the presence of an inert solvent such as dichlorobenzene, or preferably a melt of the compound of formula VII is heated with the Friedel-Crafts catalyst.

The compound of formula VII is prepared by N-acylation of a diphenylamine of formula VIII

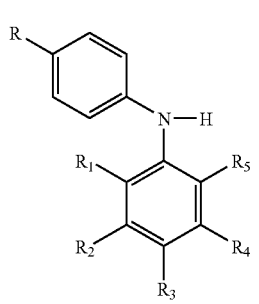

VIII wherein the symbols are as defined above with a haloacetyl chloride.

For instance, the compound of formula VIII is heated, e.g. to about 80° C., with chloroacetylchloride. The product may be recovered by diluting the reaction mixture with solvent, e.g. 2-propanol, and crystallisation.

The compound of formula VIII may be obtained by rearrangement and hydrolysis of a compound of formula IX.

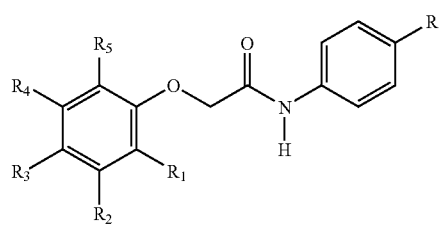

IX wherein the symbols are as defined above.

Conveniently the compound of formula IX is treated with an organic base, e.g. an alkali metal alkoxide such as sodium methoxide, preferably with heating, e.g. to a temperature of at least about 75° C. During this procedure an intermediate product of formula X,

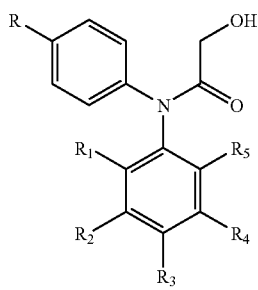

X wherein the symbols are as defined above, forms as a result of the initial rearrangement reaction, but undergoes direct cleavage under the prevailing reaction conditions to give the diphenylamine compound of formula VIII.

Alternatively the diphenylamine compound of formula VIII may be obtained by coupling of the corresponding halobenzene derivative of formula XI

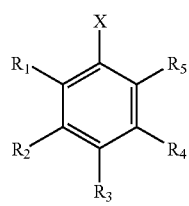

XI where X is a halogen, e.g. I or Br, and the other symbols are as defined above with p-toluidine or 4-ethyl aniline.

Such a coupling reaction may be carried out by use of Buchwald chemistry. For example, the compound of formula XI and the p-toluidine or 4-ethyl aniline are mixed with an organic base, e.g. sodium tertiary butylate, and an appropriate ligand, e.g. BINAP, in an organic solvent such as toluene; a palladium compound or catalyst precursor such as $Pd(dba)_2$ is added and the reaction mixture is heated. After cooling and treatment with acid, e.g. HCl, the diphenylamine product of formula VIII may be recovered from the organic phase of the reaction mixture.

In a further alternative, the diphenylamine compound of formula VIII may be obtained by coupling of the corresponding aniline derivative of formula IV

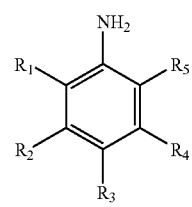

IV as defined above with 4-bromotoluene or 1-ethyl-4-bromobenzene. Such a coupling reaction may be carried out similarly by use of Buchwald chemistry. For example, the compound of formula IV and the 4-bromotoluene or 1-ethyl-bromobenzene are mixed with an organic base, e.g. sodium tertiary butylate in an organic solvent such as toluene; a palladium compound or catalyst precursor e.g. $Pd(dba)_2$, and a ligand, e.g. $P(tBu)_3$, or BINAP, are added to this reaction mixture which is then stirred at elevated temperature, e.g. 110° C., until completion of the reaction, e.g. overnight. Similarly the diphenylamine product of formula VIII may be recovered from the organic phase of the reaction mixture, for instance after cooling and treatment with acid, e.g. HCl.

The compound of formula IX may be prepared by alkylation of the corresponding phenol derivative of formula XII

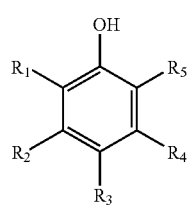

XII wherein the symbols are as defined above, with 2-chloro-N-(4-methylphenyl)acetamide or 2 chloro-N-(4-ethylphenyl)acetamide. For instance, the compound of formula XII and 2-chloro-N-(4-methylphenyl)acetamide or 2-chloro-N-(4-ethylphenyl)acetamide are mixed in an organic solvent such as 2-propanol in the presence of a base, e.g. $K_2CO_3$, and the reaction mixture boiled until completion of the reaction, e.g. for about 4 hours. 2-chloro-N-(4-methylphenyl)acetamide and 2-chloro-N-(4-ethylphenyl)acetamide may be prepared, e.g. in situ, by reaction of 4-methyl- or 4-ethylaniline with chloroacetyl chloride. The compound of formula IX may be recovered from the reaction mixture if desired. Preferably, however, the compound of formula IX is not isolated but is converted to the compound of formula VIII, by rearrangement and hydrolysis as described above carried out on the product reaction mixture resulting from the alkylation of the compound of formula XII.

Alternatively the diphenylamine of formula VIII may be prepared by oxidation of the corresponding compound of formula XIII (or tautomer thereof)

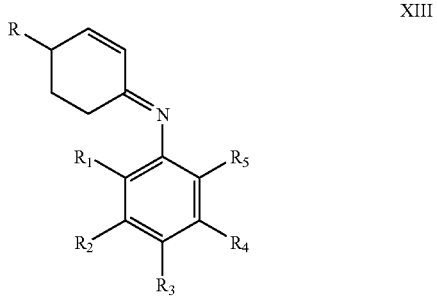

XIII wherein the symbols are as defined above.

The dehydrogenation reaction may be carried out by classical methods, for instance by treatment with iodine, e.g. $I_2$ in THF/AcOH.

The compound of formula XIII may be prepared by coupling of 1-methoxy-4-methylcyclohexa-1,4-diene or 1-methoxy-4-ethylcyclohexa-1,4-diene with an aniline derivative of formula IV as defined above.

This coupling reaction may be carried out in the presence of a catalyst such as $TiCl_4$, in organic solvents e.g. THF and chlorobenzene, preferably with cooling, e.g. at about −40° C.

1-methoxy-4-methylcyclohexa-1,4-diene or 1-methoxy-4-ethylcyclohexa-1,4-diene may be prepared by partial reduction of 4-methylanisole or 4-ethylanisole by Birch reduction, e.g. by treatment with Na in liquid ammonia, for instance as described by Subba Rao et al. *Australian Journal of Chemistry* 1992, 45, p. 187-203.

Conveniently the compound of formula XIII is not isolated, but the coupling reaction between the compound of formula IV and the 1-methoxy-4-methylcyclohexa-1,4-diene or 1-methoxy-4-ethylcyclohexa-1,4-diene, is followed by oxidation to give the diphenylamine derivative of formula VIII.

In starting compounds and intermediates, which are converted to the compounds of formulae I to XIII in a manner as hereinbefore described, functional groups present such as amino, hydroxy and carboxyl groups, are optionally protected by conventional protecting groups that are common in preparative organic chemistry. Protected hydroxy, amino and carboxyl groups are those that can be converted under mild conditions into free amino, hydroxy and carboxyl groups without other undesirable side reactions taking place. For example, hydroxy protecting groups are preferably benzyl or substituted benzyl groups.

Processes for the preparation of the 2-phenylamino-5-alkylphenylacetic acid derivatives as described above are shown schematically on the following page.

Preparation of 2-Arylamino-arylacetic acids (COX-2 inhibitors)

Overview Synthetic Methodologies

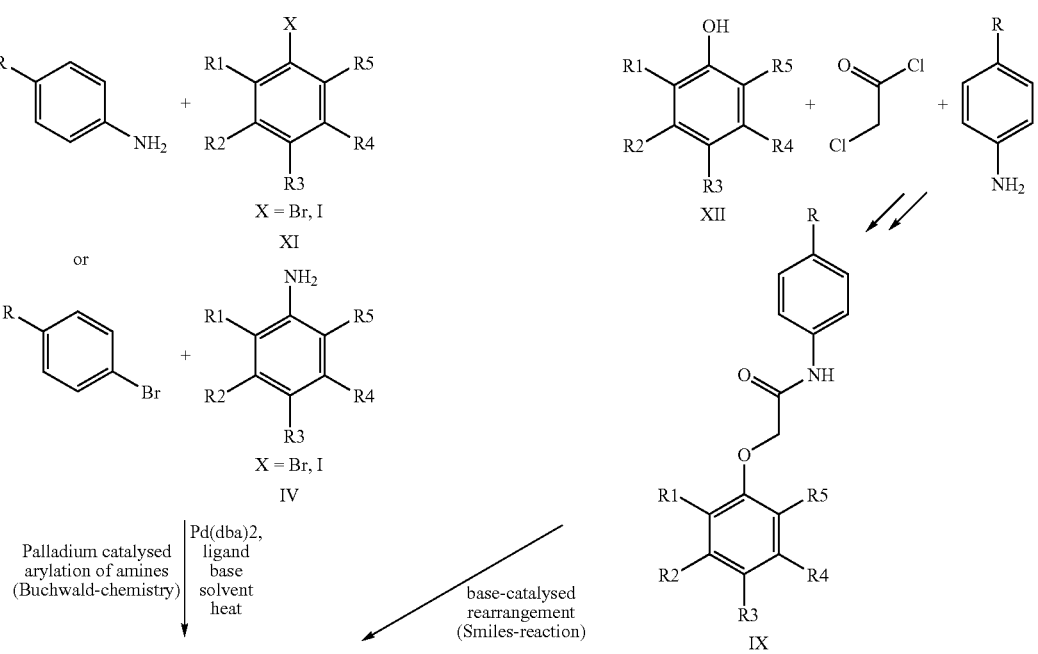

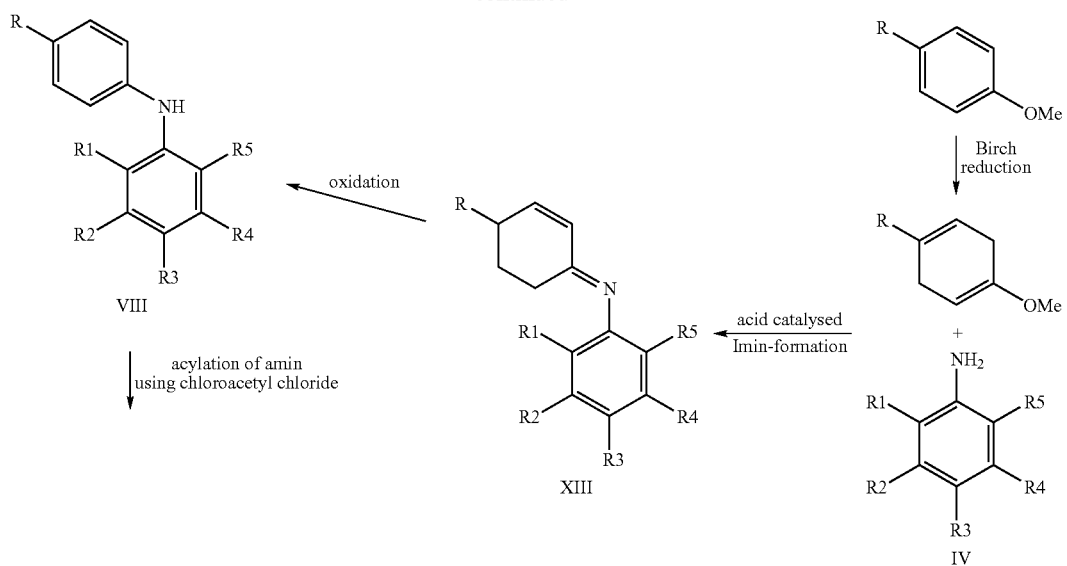
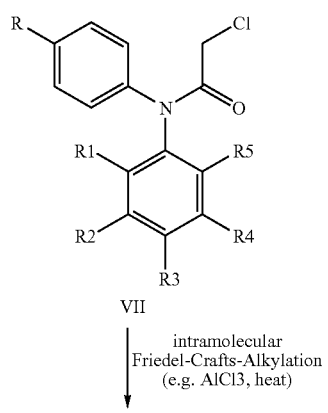
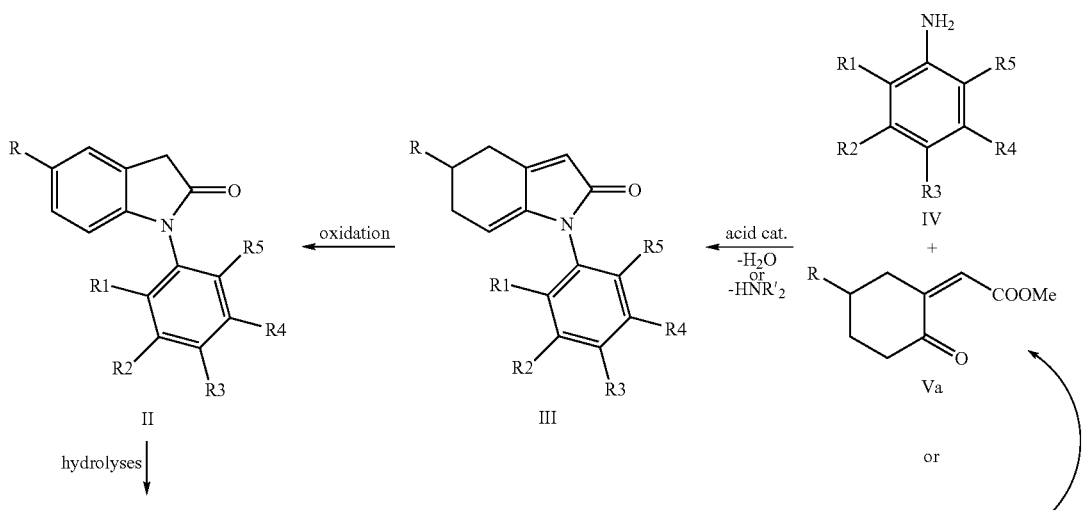

-continued

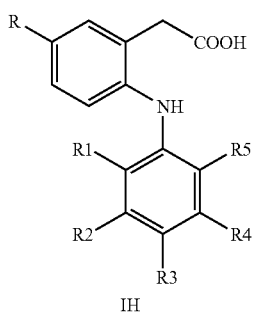
IH

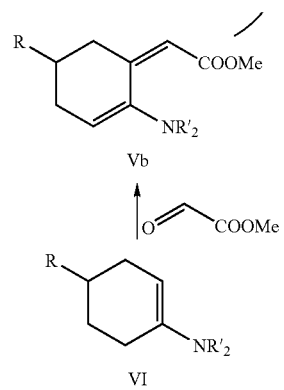
Vb

The processes for the production of the compounds of formulae II, III, VII, VIII, IX, X and XIII as described above are included within the scope of the present invention.

Thus in further aspects the invention includes a process selected from a) A process for the production of the lactam of formula II

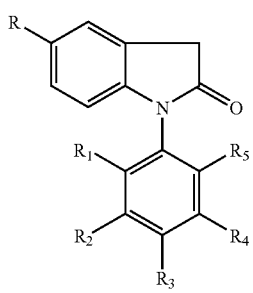
II which comprises oxidizing of a lactam of formula III

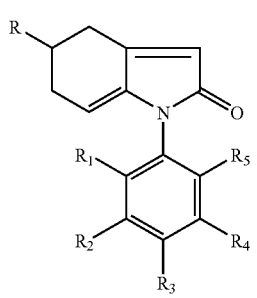
III b) A process for the production of the lactam of formula II as defined above, which comprises cyclisation of a compound of formula VII

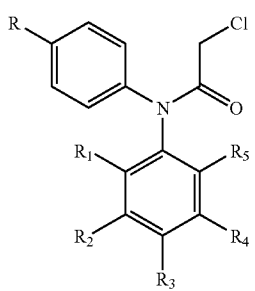
VII c) A process for the preparation of a compound of formula III as defined above comprising coupling an aniline derivative of formula IV

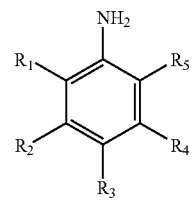
IV with a cyclohexanone derivative of formula Va or an amino substituted cyclohexene derivative of formula Vb

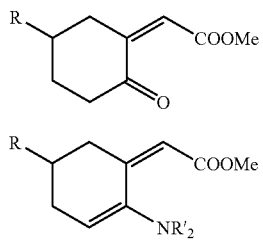
Va

Vb wherein R is ethyl or methyl and R' is lower alkyl or similar d) A process for the production of a compound of formula VII which comprises N-acylation of a diphenylamine of formula VIII

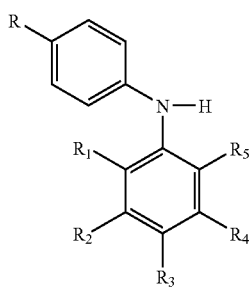
VIII with a haloacetyl chloride e) A process for the preparation of a compound of formula VIII which comprises rearrangement and hydrolysis of a compound of formula IX.

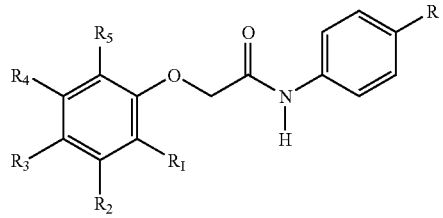

f) A process for the production of a compound of formula VIII which comprises coupling of a halobenzene derivative of formula XI

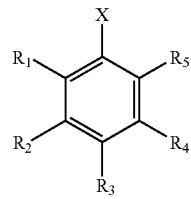

in which X is halo, with p-toluidine or 4-ethyl-aniline;

g) A process for the production of a compound of formula VII which comprises coupling an aniline derivative of formula IV with 4-bromotoluene or 1-ethyl-4-bromobenzene;

h) A process for the production of a compound of formula VIII which comprises cleavage of a compound of formula X

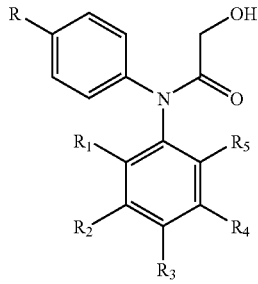

i) A process for the formation of a compound of formula X which comprises rearrangement of a compound of formula IX j) A process for the production of a compound of formula IX which comprises alkylation of a compound of formula XII with 2-chloro-N-(4-methylphenyl)acetamide or 2 chloro-N-(4-ethylphenyl)acetamide k) A process for the production of a compound of formula VIII which comprises alkylation of a compound of formula XII with 2-chloro-N-(4-methylphenyl)acetamide or 2 chloro-N-(4-ethylphenyl)acetamide followed by rearrangement and cleavage of the intermediate compound of formula IX;

l) A process for the production of a compound of formula VIII comprising oxidation of the corresponding compound of formula XIII (or tautomer thereof)

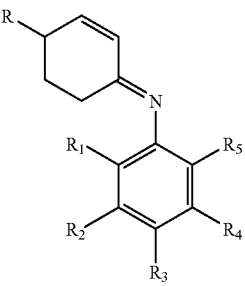

m) A process for the production of a compound of formula XIII which comprises coupling 1-methoxy-4-methylcyclohexa-1,4-diene or 1-methoxy-4-ethylcyclohexa-1,4-diene with an aniline derivative of formula IV as defined above, and n) A process for the production of a compound of formula VIII comprising coupling 1-methoxy-4-methylcyclohexa-1,4-diene or 1-methoxy-4-ethylcyclohexa-1,4-diene with an aniline derivative or formula IV, followed by dehydrogenation wherein all symbols used are as defined above.

One or more of the processes a) to n) above may be used in appropriate sequence (see the scheme given above) in the preparation of the compound of formula I.

Thus the invention further provides a process for the preparation of a compound of formula I

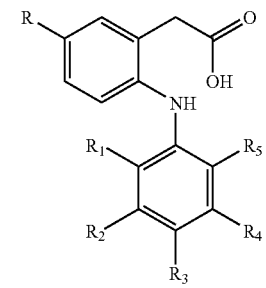

wherein the symbols are as defined above, which comprises one or more of processes selected from processes a) to n) as defined above, optionally in combination with a process according to the first aspect of the invention.

Still yet further the invention provides a compound of formula I, or a pharmaceutically acceptable salt thereof, or a pharmaceutically acceptable prodrug ester thereof, when prepared by a process which comprises one or more of processes a) to n) as defined above, preferably with a process according to the first aspect of the invention.

The compounds of formulae II, III, VII, VIII, IX, X and XIII are included per se within the scope of the present invention.

Thus in yet further aspects the invention provides a compound selected from:

a) A compound of formula II

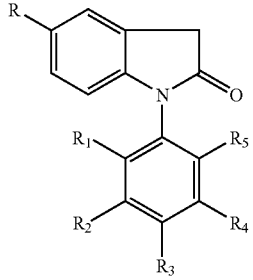

b) A compound of formula III

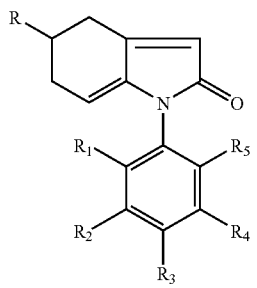

c) A compound of formula VII

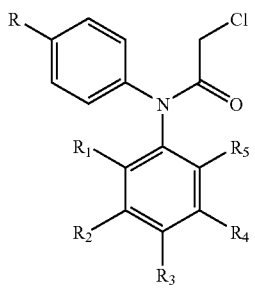

d) A compound of formula VIII

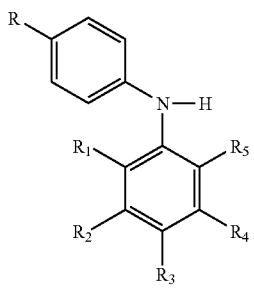

e) A compound of formula IX

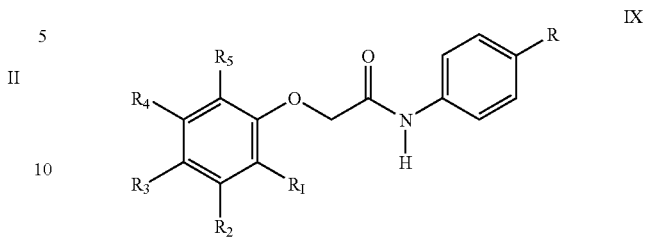

f) A compound of formula X

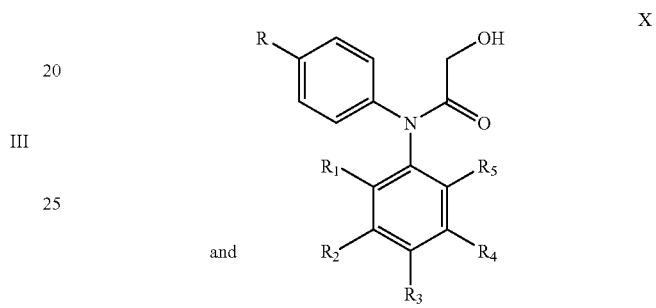

and g) A compound of formula XIII, or a tautomer thereof

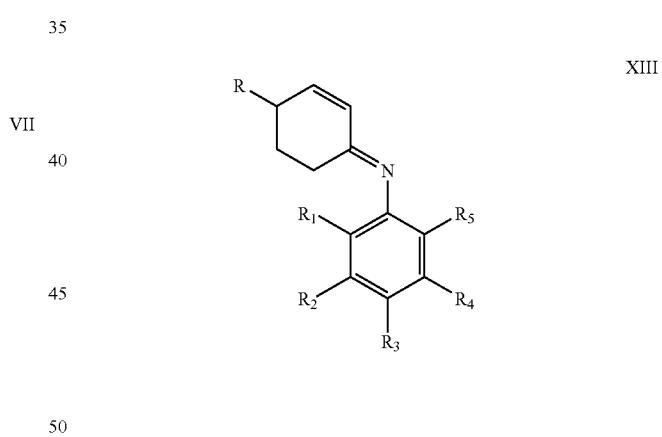

wherein the symbols are as defined above.

Compounds of formula XII in which at one of $R_1$ or $R_6$ is chlorine and the other is fluorine may be prepared by methods known in the art of chlorination of phenols, preferably in the presence of catalytic amounts of a secondary amine, e.g. diisopropylamine. In a preferred embodiment according to the present invention, the chlorination reaction comprises simultaneous addition of chlorine and phenol to the reaction mixture, preferably using hexane fraction as the solvent. It has been found that simultaneous addition of at least part, preferably the majority, of the chlorine and the phenol to the reaction mixture gives rise to high productivity and selectivity in production of the desired product as compared with the unwanted side products. Furthermore use of hexane fractions permits isolation of the desired phenol product in high purity (e.g. 99%) by crystallisation.

The invention is further described by way of illustration only in the following Examples.

EXAMPLES

The diphenylamine compounds of Formula VIII

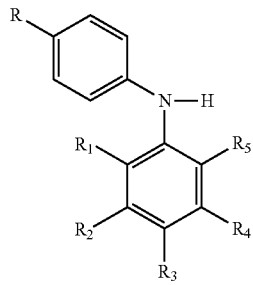

VIII are prepared by Buchwald chemistry as described below in Examples 1 and 2, either by coupling of an aniline derivative of Formula IV

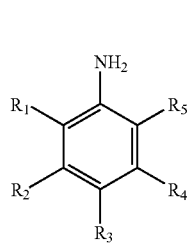

IV with 4-bromotoluene or 1-ethyl-4-bromobenzene as described in Example 1, or by coupling of a halobenzene derivative of Formula XI

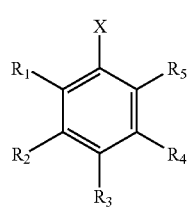

XI with p-toluidine or 4-ethylaniline as described in Examples 2. The compounds of Formula VIII thus obtained may be converted into the corresponding compounds of Formula I by procedures as described below.

Example 1a

N-(2',3',4',6'-Tetrafluorophenyl)-4-methylaniline

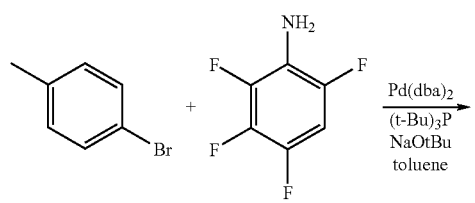

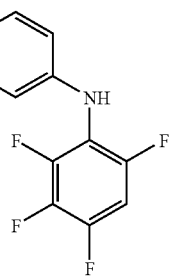

A mixture of 2,3,4,6-tetrafluoroaniline (0.72 g, 4.4 mmol), 4-bromotoluene (0.8 g, 4.7 mmol), toluene (55 ml), sodium tert-butoxide (0.8 g, 8.3 mmol), tri-tert-butylphosphine (130 mg, 0.64 mmol) and bis-dibenzylideneacetone-palladium(0) (125 mg, 0.2 mmol) is heated under nitrogen to 85° C. for 3 h. After cooling, water (50 ml), concentrated aqu. HCl (10 ml) and hyflo (1 g) is added and stirring is continued for about one hour followed by filtration. The organic phase is washed with water twice, evaporated and the residue is subjected to flash chromatography on silica (45 g) using heptane/toluene (2:1) as the eluent to afford N-(2',3',4',6'-Tetrafluorophenyl)-4-methylaniline (0.92 g, 3.6 mmol) as an oil which crystallises (mp. 64-65° C.).

$^1$H-NMR (400 MHz, DMSO-d6): 2.20 (s, 3H, CH$_3$); 6.63 [d, 8.2 Hz, 2H, HC (2), HC (6)]; 6.99 [d, 8.2 Hz, 2H, HC (3), HC (5)]; 7.56 [symmetrical m, 1H, HC (5')]; 7.84 (s, 1H, NH).

N,N-Bis-p-tolyl-2,3,4,6-tetrafluoroaniline is isolated as a byproduct, mp: 94.96° C.

Example 1b

N-(2',3',5',6'-Tetrafluorophenyl)-4-ethylaniline

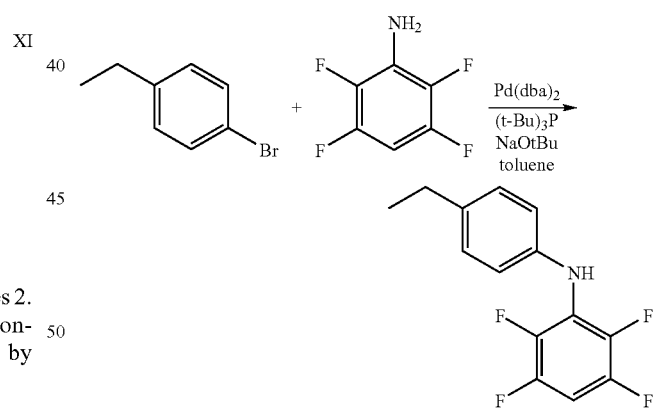

A mixture of 2,3,5,6-tetrafluoroaniline (4.5 g, 27.3 mmol), 4-ethylbromobenzene (5.0 g, 27 mmol), toluene (50 ml), sodium tert-butoxide (4.67 g, 48 mmol), tri-tert-butylphosphin (217 mg, 1.07 mmol) and bis-dibenzylideneacetone-palladium(0) (260 mg, 0.45 mmol) is heated under nitrogen to 85° C. for 15.5 h. The mixture is cooled to room temperature and water (30 ml), concentrated hydrochloric acid (20 ml) and hyflo are added. After stirring for 45 minutes, the mixture is filtered and the organic phase is washed with water three times. The solvent is evaporated in vacuo and the residue is chromatographed on silica using hexane/toluene (9:1 to 3:1) affording N-(2',3',5',6'-tetrafluorophenyl)-4-ethylanilin as a liquid.

$^1$H-NMR (400 MHz, CDCl$_3$): 1.26 (t, 3H, CH$_3$); 2.65 (q, 2H, CH$_2$); 5.65 (s, 1H, NH); 6.73 [tt, 1H, H—C (4')]; 6.88 [d, 2H, H—C (2,6)]; 7.15 [d, 2H, H—C (3,5)].

MS, m/z: 268 (M-H), 248 (M-HF).

Example 1c

N-(2'-Chloro-4'-fluoro-6'-methylphenyl)-4-methylaniline

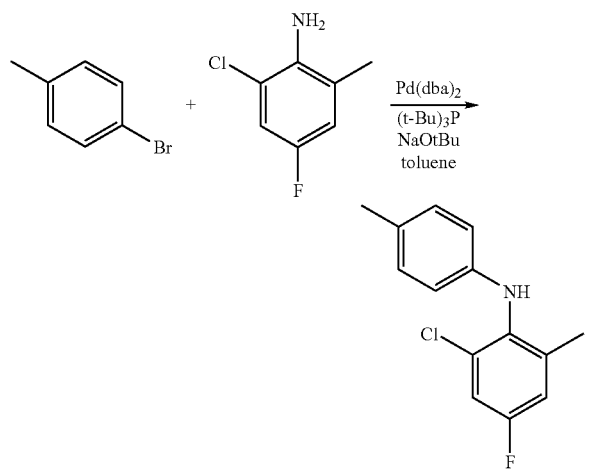

308 g (19.3 mmol) of 2-chlor-4'-fluoro-6-methyl-aniline (prepared from N-acetyl-4-fluoro-2-methylaniline by chlorination followed by hydrolyses), 3.48 g (20.3 mmol) of 4-bromotoluene are dissolved in 55 ml of toluene and after the addition of 3.43 g (36 mmol) of sodium tert-butoxide, 166 mg (0.82 mmol) of tri-tert-butylphosphin and 460 mg (0.8 mmol) of bis-dibenzylideneacetone-palladium(0), the mixture is heated with stirring under nitrogen to 90° C. for 40 minutes. The usual aqueous acidic workup (50 ml water, 10 ml conc. HCl, 1 g hyflo, filtration, washing the organic phase with water, drying, evaporation) gave 5.5 g of the crude product which may be purified by flash-chromatography using silica and heptane as the eluent affording 3.52 g of N-(2'-chloro-4'-fluoro-6'-methylphenyl)-4-methylaniline as an oily substance.

$^1$H-NMR (400 MHz, DMSO-d6): 2.18 (s, 3H, CH3); 6.37 (d, 2H, H—C (2,6)]; 6.92 [d, 2H, H—C (3,5)]; 7.19 (dd, 1H, H—C (5')]; 7.32 (s, 1H, NH); 7.35 (dd, 1H, HC (3')].

Example 1d

N-(2'-Chloro-6'-methylphenyl)-4-methylaniline

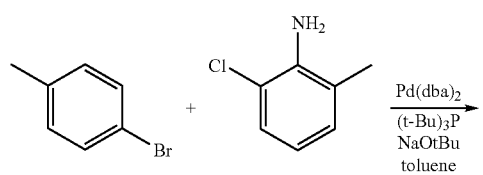

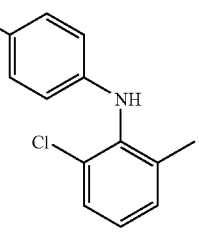

1.02 g (7.2 mmol) of 2-chloro-6-methylaniline, 1.23 g (7.2 mmol) 4-bromotoluene, 1.15 g (12 mmol) sodium tert-butoxide, 160 mg (0.7 mmol) tri-tert-butyhphosphine and 130 mg (0.23 mmol) bis-dibenzylideneacetone-palladium(0) are reacted in 50 ml toluene under nitrogen at 90° C. for 20 minutes and at 60° C. over night. Aqueous workup (3N HCl, with hyflo, washing the organic phase with water) and flash-chromatography on silica using heptan/toluene (4:1) as the eluent affords 1.49 g of N-(2'-chloro-6'-methylphenyl)-4-methylaniline.

$^1$H-NMR (400 MHz, CDCl$_3$): 2.21 (s, 3H, C-6'-CH$_3$); 2.29 (s, 3H, C-4-CH$_3$); 5.61 (s, br, 1H, NH); 6.57 [d, 2H, HC (2,6)]; 7.04 [d, 2H, HC (3,5)]; 7.07 [t under signal at 7.04, 1H, HC (4')]; 7.16 [d, 2H, H(C5')]; 7.33 [d, 1H, H(C3')].

N,N-Bis-p-tolyl-2-chloro-6-methylaniline (9 mg) is isolated as a byproduct.

Example 1e

N-(2'-Chloro-6'-methylphenyl)-4-ethylaniline

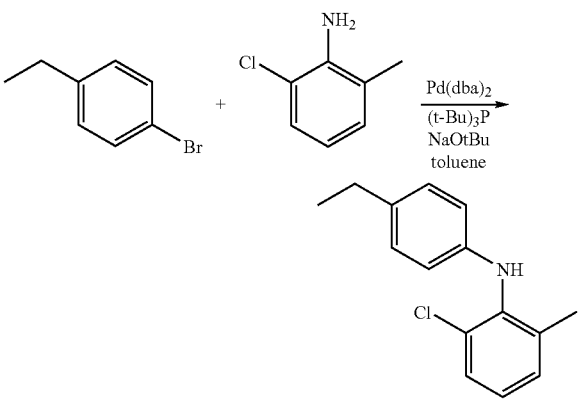

To a solution of 5.2 g (37 mmol) of 2-chloro-6-methylaniline and 6.95 g (37.6 mmol) of 4-ethyl bromobenzene in 50 ml of toluene is added 6.5 g (68 mmol) sodium tert-butoxide, 180 mg (0.89 mmol) tri-tert-butylphosphine (dissolved in 2 ml of toluene) and 300 mg (0.52 mmol) of bis-dibenzylideneacetone palladium(0). The mixture is heated under nitrogen to 90° C. for 3 hours and then cooled to room temperature. Hyflo (1 g), water (30 ml) and conc, hydrochloric acid (10 ml) are added and after stirring for 30 minutes the mixture is filtered. The organic phase is washed with water (30 ml) twice and evaporated. The residue is subjected to flash-chromatography on silica (75 g) during with heptane to afford 5.3 g (21.6 mmol. 58%) of N-(2'-chloro-6'-methylphenyl)-4-ethylaniline as an almost colourless liquid.

$^1$H-NMR (300 MHz, CDCl$_3$): 1.10 (t, 3H, CH$_3$—CH$_2$—); 2.10 [s, 3H, CH3-C (6')]; 2.50 (q, 2H, CH$_3$—$\overline{CH_2}$—); 5.54 (s, br, 1H, NH); 6.48 [d, 2H, HC (2,6)]; 6.93 [t, $\overline{1H, H}$(C4')]; 6.95 [d, 2H, HC (3,5)]; 7.05 [d, 1H, HC (5')]; 7.22 (d, 1H, HC (3')].

Example 1f

N-(2',4'-Dichloro-6'-methylphenyl)-4-ethylaniline

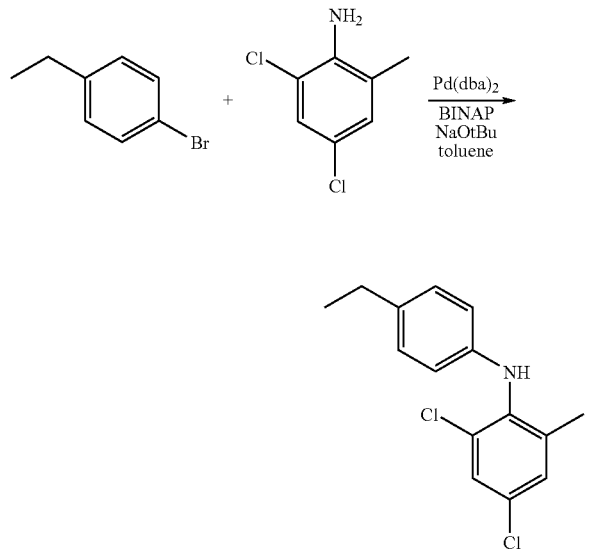

The mixture of 2,4-dichloro-6'-methylaniline (3.313 g, 18.8 mmol), 4-ethyl bromobenzene (3.64 g, 20 mmol), sodium tert-butoxide (3.41 g, 35 mmol), racemic BINAP (0.274 g, 0.44 mmol), bis-dibenzylideneacetone-palladium (0) (250 mg, 0.43 mmol) and toluene (50 ml) is refluxed under nitrogen for 22 h. The mixture is cooled, treated with water (40 ml), conc. HCl (10 ml), hyflo (1.7 g) stirred for additional 30 minutes and filtered. The organic phase is washed with water twice and evaporated. The crude product (6.88 g) is purified by flash-chromatography (silica, toluene) to afford 2.93 g of N-(2',4'-dichloro-6'-methylphenyl)-4-ethylaniline.

$^1$H-NMR (300 MHz, CDCl$_3$): 1.15 (t, 3H, CH$_3$—CH$_2$—Ar); 2.08 (s, 3H, C-6'-CH3); 2.50 (q, 2H, $\overline{CH_3}$—CH$_2$—Ar); 5.42 (s, br., 1H, NH); 6.50 [d, 2H, HC (2,6,)]; $\overline{6.96}$ [d, 2H, HC (3,5)]; 7.10 [s, 1H, HC (5')]; 7.25 [s, 1H, HC (3')].

The reaction proceeds much faster even at 85° C. when BINAP is replaced by tri-tert-butylphosphine; however N,N-di-(4-ethylphenyl)-2',4'-dichloro-6'-methylaniline is formed as a byproduct in considerable amounts when excess of 4-ethyl bromobenzene is used. This byproduct can be isolated as a solid, mp: 74-75° C.; $^1$H-NMR (400 MHz, CDCl$_3$): 1.24 (t, 6H, CH$_2$—CH$_3$); 2.09 (s, 3H, C-6'-CH$_3$); 2.61 (q, 4H, CH$_2$—CH$_3$); $\overline{6.89}$ [d, 4H, HC (2,6)]; 7.06 [d, 4H, HC (3,5)]; $\overline{7.20}$ [s, 1H, HC (5')]; 7.36 [s, 1H, HC (3')]; MS: 383 (M+), 368 (M-CH$_3$), 354 (M-CH$_2$CH$_3$).

Example 2

N-(2',3',6'-Trifluorophenyl)-4-ethylaniline

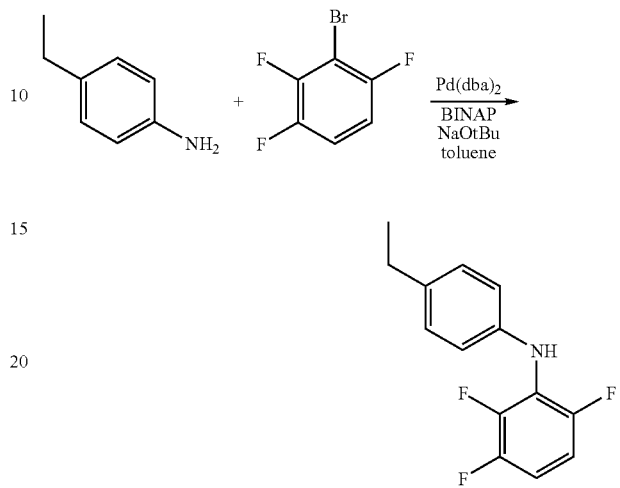

To a solution of 1.21 g of 4-ethylaniline, 1.10 g of 2,3,6-trifluoro-bromobenzene in 10 g of toluene is added consecutively 350 mg BINAP and 300 mg of bis-dibenzylideneaceton-palladium (0) [Pd(dba)$_2$] in 3 ml of toluene and 0.9 g of sodium tert.-butoxide in 3 ml toluene. The mixture is flushed with nitrogen and heated for 6 h under reflux. After cooling to room temperature, water (30 ml), concentrated hydrochloric acid (10 ml) and hyflo (1 g) are added and stirring is continued for 1 h. The mixture is filtered and the filtrate is separated into its phases. The organic phase is washed three times with water, dried using magnesium sulfate and evaporated to dryness. The residue can be used as such in the following step or purified by flash chromatography on silica using toluene as the eluent affording 1.13 g of N-(2',3',6'-trifluorophenyl)-4-ethylanilin.

$^1$H-NMR (300 MHz, CDCl$_3$): 1.14 (t, 7.7 Hz, 3H, CH$_3$—CH$_2$—Ar); 2.53 (q, 7.7 Hz, 2H, CH$_3$—CH$_2$—Ar); $\overline{5.29}$ (br. s, 1H, NH); 6.7-6.81 [m, 2H, C-4'-H, $\overline{HC(5')}$]; 6.75 [d, 2H, HC (2,6)]; 7.02 [d, 8.5 Hz, 2H, HC (3,5)].

Diphenylamine compounds of Formula VIII, for instance as prepared above in Examples 1 and 2, are converted to the corresponding compounds of Formula VII

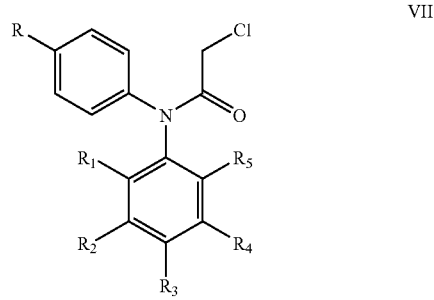

as described in Example 3

Example 3a

N-(2',3',4',6'-Tetrafluorophenyl)-N-chloroacetyl-4-methylaniline

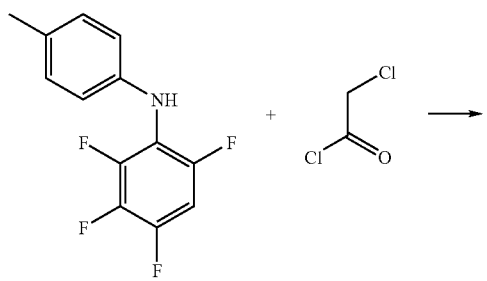

The mixture of N-(2',3',4'6'-tetrafluorophenyl)-4-methylanilin (0.82 g, 3.2 mmol) and chloro acetylchloride (1.6 g) is heated with stirring to 90° C. under nitrogen for 1.3 h. To destroy excess of the acid chloride, 2-propanol and water (2 ml each) is added and stirring is continued over night at room temperature. After adding toluene (20 ml), the mixture is extracted with sodium bicarbonate and the organic phase is dried with magnesium sulfate and evaporated to dryness. The residue is purified by flash chromatography (silica, toulene) to obtain N-(2',3',4',6'-tetrafluorophenyl)-N-chloroacetyl-4-methylaniline (0.98 g, 2.95 mmol) as an oil.

Example 3b

N-(2',3',5',6'-Tetrafluorophenyl)-N-chloroacetyl-4-ethylaniline

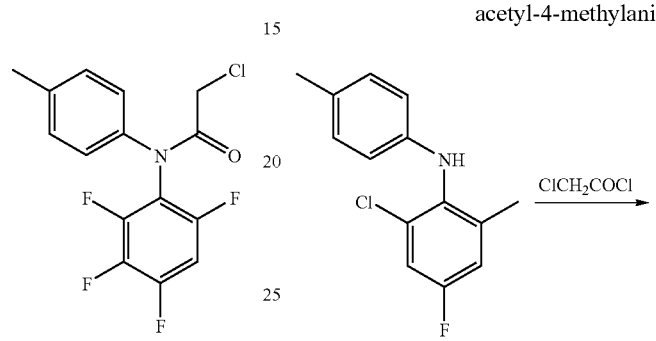

N-(2',3',5',6'-tetrafluorophenyl)-4-ethylanilin (2.05 g) and chloro acetylchloride (1.99 g) is mixed without solvent and heated with stirring to 90° C. under nitrogen for 20 h. Tetrahydrofurane (10 ml) and aqueous sodium bicarbonate are added after cooling and stirring is continued for about 1 hour.

The organic phase is diluted with toluene and washed with water three times and dried over magnesium sulfate. Evaporation and chromatography of the residue (silica, toluene) gave N-(2',3',5',6'-tetrafluorophenyl)-N-chloroacetyl-4-ethylaniline (1.84 g) as a solid which is recrystallised from heptane, mp.: 72° C.

$^1$H-NMR (400 MHz, DMF-d7, 140° C.): 1.25 (t, 3H, CH$_3$); 2.70 (q, 2H, CH$_2$); 4.28 (s, 2H, CH$_2$—CO); 7.35 [d, 2H, HC (3,5)]; 7.43 [d, 2H, HC (2,6)]; 7.65 [tt, 1H, HC (4')].

Example 3c

N-(2'-Chloro-4'-fluoro-6'-methylphenyl)-N-choroacetyl-4-methylaniline

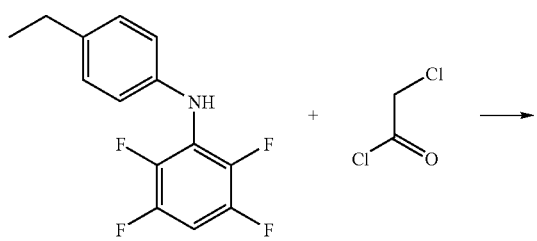

1.32 g of N-(2'-Chloro-4'-fluoro-6'-methylphenyl)-4-methylaniline is reacted with chloracetylchloride (1.76 g) at 90° C. for 30 minutes. The cooled mixture is stirred with toluene (20 ml) and aqu. sodium carbonate for 30 minutes and the organic phase is evaporated. The residue is purified flash-chromatography on silica using toluene affording 1.04 g of N-(2'-chloro-4'-fluoro-6'-methylphenyl)-N-chloroacetyl-4-methylaniline as a solid which is recrystallised from heptane/2-propanol (9:1), mp.: 96-97° C.

$^1$H-NMR (400 MHz, DMF-d7, 120° C., all peaks appear broadend or split): 2.43 (s, 3H, CH$_3$); 4.31 (s, 2H, Cl—CH$_2$—CO); 7.31 [d, 1H, HC (5')]; 7.32 and 7.40 [AB, 4H, C—HC (2,6) and HC (3,5)]; 7.45 [s, 1H, HC (3')].

Example 3d

N-(2'-Chloro-6'-methylphenyl)-N-chloroacetyl-4-methylaniline

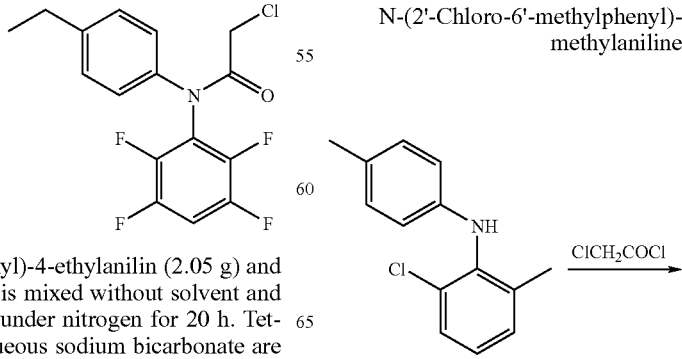

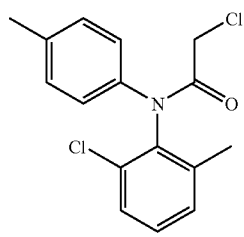

The solution of N-(2'-chloro-6'-methylphenyl)-4-methylaniline (1.4 g) in 2.21 g chloroacetylchloride is heated to 90° C. for 4 h. The mixture is diluted with toluene (25 ml), cooled to room temperature and washed with aqu. sodium carbonate. The organic phase is dried, evaporated and the residue is subjected to flash chromatography [57 g silica, toluene and toluene/ethylacetate (98:2)] to afford 1.45 g of N-(2'-Chloro-6'-methylphenyl)-N-chloroacetyl-4-methylaniline which is crystallised from heptane, mp: 113-114° C.

Example 3e

N-(2'-Chloro-6'-methylphenyl)-N-chloroacetyl-4-ethylaniline

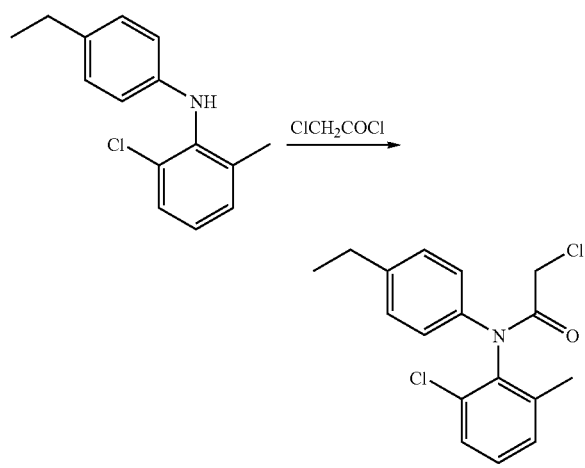

N-(2'-Chloro-6'-methylphenyl)-N-4-ethylaniline (4.95 g, 20 mmol) is treated with chloro acetylchloride (3.23 g, 28.5 mmol) and the mixture is heated with stirring under nitrogen at 95° C. for 40 minutes. After adding 2-propanol (5 ml) and cooling to room temperature, the mixture is diluted with toluene and extracted with aqu. sodium bicarbonate. The organic phase is washed with water and evaporated to dryness. Flash chromatography on silica (55 g) using toluene as the eluent affords 5.66 g (17.6 mmol, 88%) of N-(2'-chloro-6'-methylphenyl)-N-chloroacetyl-4-ethylaniline as a viscous liquid.

$^1$H-NMR (400 MHz, DMF-d7, 140° C.): 1.22 (t, 3H, $CH_3$—$CH_2$—), 2.32 (s, 3H, $CH_3$—C6'); 2.65 (q, 2H, $CH_3$=$CH_2$—); 4.12, 4.18 (AB, 2H, $CH_2$—Cl); 7.22 and 7.31 [each d, each 2H, HC (2,6) and HC (3,5)]; 7.3-7.5 [m, 3H, HC (3',4',5')].

Example 3f

N-(2',4'Dichloro-6'-methylphenyl)-N-chloroacetyl-4-ethylaniline

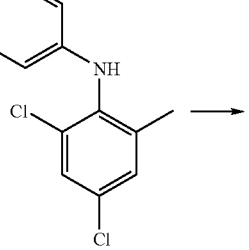

N-(2',4'Dichloro-6'-methylphenyl)-4-ethylaniline (4.83 g as a mixture with the byproduct N,N-di-(4-ethylphenyl)-2',4'-dichloro-6'-methylaniline) is dissolved in 4.18 g of chloro acetylchlorid and heated to 100° C. for 1.5 h. The mixture is cooled, diluted with toluene (50 ml) and extracted with aqu. sodium bicarbonate. The organic phase is evaporated to dryness and chromatographed on silica (75 g) eluting with toluene to afford unreacted N,N-di-(4-ethylphenyl)-2',4'-dichloro-6'-methylaniline and N-(2',4-dichloro-6'-methylphenyl)-N-chloroacetyl-4-ethylaniline (2.95 g). A crystallised sample melts at 83-84° C.

$^1$H-NMR (400 MHz, DMF-d7, 140° C.): 1.22 (t, 3H, $CH_3$—$CH_2$): 2.31 (s, 3H, C-6'-CH3); 2.56 (q, 2H, $CH_3$=$CH_2$); 4.20 (s, split, 2H, Cl—$CH_2$—CO); 7.35, 7.42 [AB, 4H, HC (2,6) and HC (3,5) respectively]; 7.40 [s, br. 1H, HC (5')], 7.53 [s, br, 1H, HC (3')].

Alternatively compounds of Formula VIII may be prepared by a procedure involving coupling of 1-methoxy-4-methylcyclohexa-1,4-diene or 1-methoxy-4-ethylcyclohexa-1,4-diene with an aniline derivative of formula IV as defined above to give an intermediate compound of Formula XIII (or tautomer thereof)

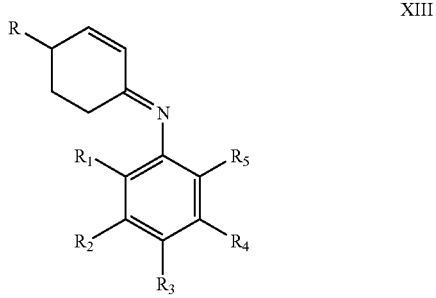

which is oxidised without isolation to give the compound of Formula VIII, as described below in Example 4.

Example 4a)

N-(2',6'-Dichlorophenyl)-4-methylaniline

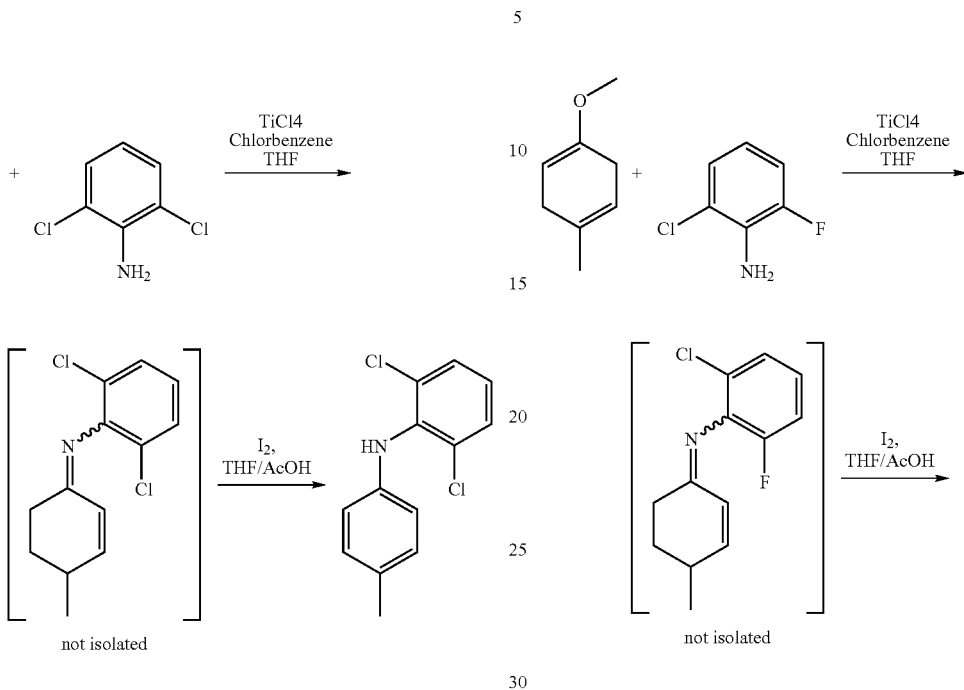

not isolated a) A solution of 4.35 g 2,6-dichloro-aniline in 4 ml of tetrahydrofuran and 35 ml of chlorobenzene is cooled down to −40 to −45° C. At this temperature, 5.09 g of titanium-tetrachloride is added to the solution, followed by the addition of 5.0 g of 1-Methoxy-4-methylcyclohexa-1,4-diene. The reaction mixture is allowed to warm up to approximately −35° C. and stirred for 2 hours at this temperature. A solution of 10.18 g of iodine in 20 ml of tetrahydrofuran and 2.3 ml of acetic acid is then added dropwise to the reaction mixture and the temperature was allowed to warm up to 0° C. The mixture was stirred for 1 hour at 0° C. and 16 hours at 25° C. Then 3.4 g of iodine is added to the reaction mixture and stirring is continued for additional 24 hours at 25° C. The reaction is finally quenched by pouring the reaction mixture onto a mixture of 250 ml of aqueous Sodium bisulfite (38-40%) and 400 ml of saturated aqueous sodium carbonate. The water phase is extracted with ethyl acetate (1×200 ml and 2×100 ml), the ethyl acetate phases are unified and washed with 100 ml of water. The organic phase was dried over anhydrous sodium sulfate and evaporated in vacuo to yield 11.44 g of a dark slurry. The slurry was dissolved in hexane/t-butyl-methyl-ether and the solution was filtered over silica gel to obtain, after evaporation of the solvent, 5.75 g of erode product. The product can be used directly in the next step. Alternatively, h can be purified e.g. by column chromatography on silica gel with hexane/t-butyl-methylether (9:1) as eluent to yield pure N-(2',6'-Dichlorophenyl)-4-methylaniline.

$^1$H-NMR (CDCl$_3$, 400 MHz, 300K) δ 2.31 (s, 3H, CH$_3$), 3.6-4.8 (broad signal, 1H, NH), 6.68 (d, J=8 Hz, 2H, H—C (2) and H—C (6)), 7.02-7.12 (m, 3H, H—C (3), H—C (5) and H—C (4')), 7.38 (d, J=8 Hz, 2H, H—C (3') and H—C (5')).

MS (EI): m/z 251 (M$^+$), 216 (M-Cl)$^+$, 181 (M-2Cl)$^+$

Example 4b)

N-(2'-Chloro-6'-fluoro-phenyl-4-methylaniline not isolated

A solution of 3.91 g 2-chloro-6-fluoro-aniline in 4 ml of tetrahydrofuran and 35 ml of chlorobenzene is cooled down to −40 to −45° C. At this temperature, 5.09 g of titanium-tetrachloride is added to the solution, followed by the addition of 5.0 g of 1-Methoxy-4-methylcyclohexa-1,4-diene. The reaction mixture is allowed to warm up to approx. −35° C. and stirred for 2 hours at this temperature. A solution of 10.18 g of iodine in 20 ml of tetrahydrofuran and 2.3 ml of acetic acid is then added drop-wise to the reaction mixture and the temperature was allowed to warm up to 0° C. The mixture was stirred for 1 hour at 0° C. and 16 hours at 25° C. Then 3.4 g of iodine is added to the reaction mixture and stirring is continued for additional 24 hours at 25° C. The reaction is finally quenched by pouring the reaction mixture onto a mixture of 250 ml of aeq. Sodium bisulfite (38-40%) and 400 ml of saturated aeq. sodium carbonate. The aqueous phase is extracted with ethyl acetate (1×200 ml and 2×100 ml), the ethyl acetate phases are unified and washed with 100 ml of water. The organic phase was dried over anhydrous sodium sulfate and evaporated in vacuo to give a yellow viscous liquid. The liquid was dissolved in hexane/t-butyl-methyl-ether and the solution was filtered over silica gel to obtain, after evaporation of the solvent, 4.33 g of crude product. The product can be used directly in the next step. Alternatively, it can be purified e.g. by column chromatography on silica gel with hexane/t-butyl-methylether (9:1) as eluent to yield pure N-(2'-chloro-6'-fluoro-phenyl)-4-methylaniline.

$^1$H-NMR (DMSO-d$^6$, 500 MHz, 300K) δ 2.17 (s, 3H, CH$_3$); 6.53 [dd, J=8.5 Hz, J$_{H-F}$=1.5 Hz, 2H, HC (2) and HC (6)], 6.94 [d, J=8.0 Hz, 2H, HC (3) and HC (5)]. 7.16 [ddd, J=8.0 Hz, J$_{H-F}$=6.0 Hz, 1H, HC (4')], 7.25 [ddd, J=8.0, 1.5 Hz, J$_{H-F}$=8.0, 1H, HC (5')]; 7.34 [ddd, J=8.0, 1.5 Hz, J$_{H-F}$=1.5, 1H, HC (3')]; 7.63 (s, 1H, NH).

MS(EI) m/z 235 (100, M$^+$), 200 (35, (M-Cl)$^+$), 185 (55)

Example 4c)

N-(2'-Chloro-6'-methyl-phenyl-4-ethylaniline

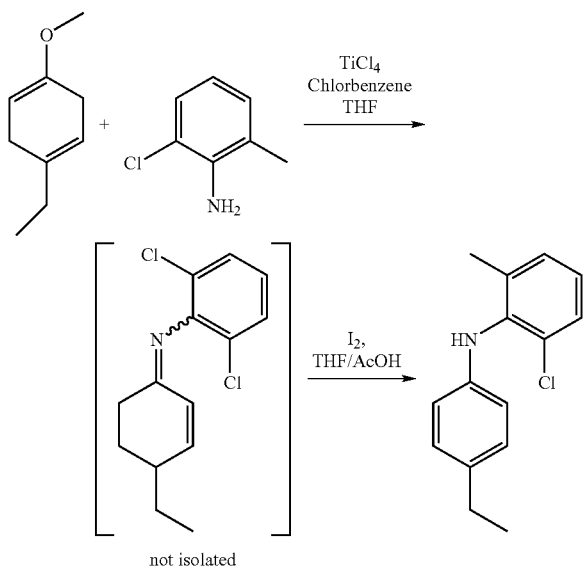

not isolated

A solution of 3.0 g 2-Chloro-6-methyl-aniline in 3.5 ml of tetrahydrofuran and 31 ml of chlorobenzene is cooled down to −40 to −45° C. At this temperature, 4.01 g of titanium-tetrachloride is added to the solution, followed by the addition of 6.18 g of 1-Methoxy-4-ethylcyclohexa-1,4-diene. The reaction mixture is allowed to warm up to approx. −35° C. and stirred for 3 hours at this temperature. A solution of 8.06 g of iodine in 16.4 ml of tetrahydrofuran and 1.8 ml of acetic acid is added to the reaction mixture and the temperature is allowed to warm up to 0° C. The mixture is stirred for 30 minutes at 0° C. and 2 hours at 25° C. Then 2.68 g of iodine is added to the reaction mixture and stirring is continued for additional 24 hours at 25° C. Again, 2.68 g of iodine is added and stirring is continued for additional 72 hours at 25° C. The reaction is finally quenched by pouring the reaction mixture onto a mixture of 250 ml of aqueous sodium bisulfite (38-40%) and 450 ml of saturated aqueous sodium carbonate. The water phase is extracted with ethyl acetate (1×200 ml and 2×100 ml), the ethyl acetate phases are unified and washed with 100 ml of brine. The organic phase was dried over anhydrous sodium sulfate and evaporated in vacuo to give a dark viscous liquid. The liquid was dissolved in heptane/toluene and the solution was filtered over silicagel to obtain, after evaporation of the solvent, 2.0 g of crude product. The product can be used directly in the next step. Alternatively, it can be purified e.g. by column chromatography on silica gel with heptane/toluene (7:3) as eluent to yield pure N-(2'-Chloro-6'-methyl-phenyl)-4-ethylaniline.

$^1$H-NMR (CDCl$_3$, 400 MHz, 300K) δ 1.24 (t, J=7.5 Hz, 3H, H$_3$C (8)), 2.22 (s, 3H, H$_3$C—C (2')), 2.61 (q, J=7.5 Hz, 2H, H$_2$C (7)), 4.0-5.5 (broad signal, 1H, NH), 6.60 (d-like, J=8 Hz, 2H, H—C (2) and H—C (6)), 7.02-7.10 (m, 3H, H—C (3), H—C (5) and H—C (4')), 7.10-7.20 (m, 1H, H—C (3')), 7.33 (d-like, J=9 Hz, 1H, H—C (5')).

MS: m/z 245 (M$^+$), 230, 214, 194, 180.

The 1-Methoxy-4-methylcyclohexa-1,4-diene and 1-Methoxy-4-ethylcyclohexa-1,4-diene starting materials for Example 4 are prepared according to a known literature procedure.

1-Methoxy-4-methylcyclohexa-1,4-diene (

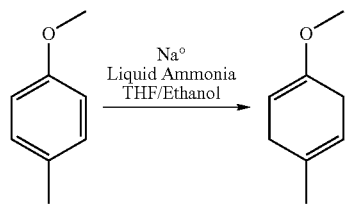

Preparation according to a known literature procedure:
G. S. R. Subba Rao, D. K. Banerjee, L, Uma Devi and Uma Sheriff, Australian Journal of Chemistry 1992, 45, p. 187-203

1-Methoxy-4-ethylcyclohexa-1,4-diene

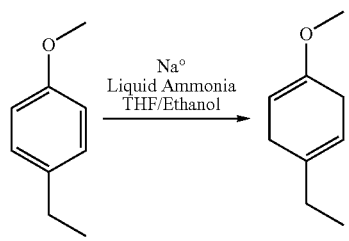

Compound 4 was prepared according to the same literature procedure given above for 1-methoxy-4-methylcyclohexa-1,4-diene.

The products of Examples 4 are converted into the corresponding compounds of Formula VII for instance as described in Examples 3 above and 5 below

Example 5

N-(2',6'-Dichlorophenyl)-N-chloroacetyl-4-methylaniline

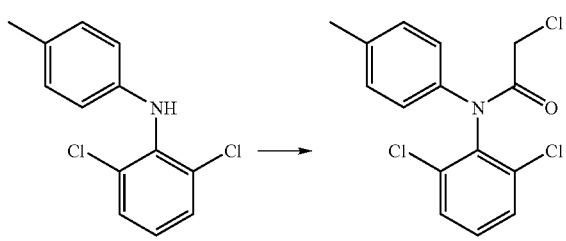

N-(2',6'-Dichlorophenyl)-4-methylaniline (4.86 g) is reacted with chloroacetylchloride (3.92 g) at 90° C. for 2 h. After dilution with toluene, the mixture is washed with aqueous sodiumcarbonate twice, 40% aqu. sodium bisulfite and water. The organic phase is dried (MgSO4) and evaporated.

The residue is recrystallised from ethanol (12 g) to obtain N-(2',6'-Dichlorophenyl)-N-chloroacetyl (2.83 g), mp: 129.5-130° C.

In a yet further alternative compounds of Formula VII may be prepared by a procedure involving a Smiles type rearrangement of a compound of Formula IX

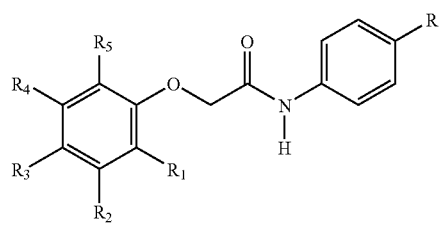

to give an intermediate product of Formula VIII as defined above which is converted without being isolated to the compound of Formula VII as described in Example below.

Example 6a)

N-(2',6'-dichloro-4'-methylphenyl)-N-chloroacetyl-4-methylaniline

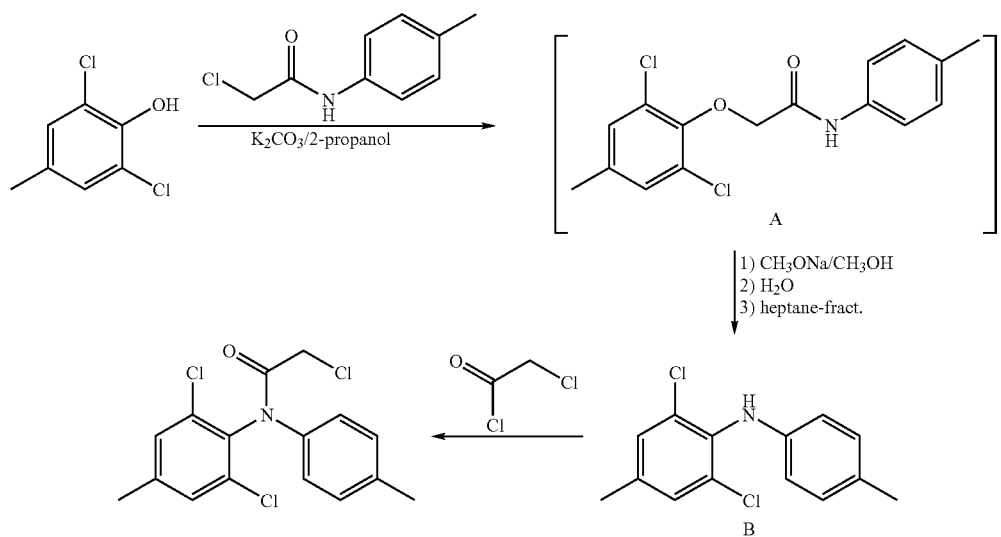

12 g (67 mmol) of 2,6-dichloro-4-methylphenol are dissolved in 25 ml of 2-propanol followed by the addition of 10.5 g (76 mmol) of potassium carbonate and 12.8 g (70 mmol) of 2-chloro-N-(4-methylphenyl)acetamide. The mixture is refluxed for 4 h. At this time, the formation of A: 2-(2',6'-dichloro-4'-methylphenoxy)-N-(4-methylphenyl)acetamide is completed. 13.6 ml of sodium methylate solution 30% in methanol are slowly added and the temperature is increased to about 85° C. by distilling 25 ml of solvent. The mixture is stirred 2 h more to complete the formation of B. 25 ml of water are added at 70° C. to obtain a 2 phases solution. The lower layer is discarded. The upper layer is diluted with 20 ml of heptane-fraction and washed with 2×20 ml of water. The organic phase is separated and concentrated in vacuo to obtain N-(2',6'-dichloro-4'-methylphenyl)-4-methylaniline as a crude oil. GC/MS: 265 (100, M+), 195 (130).

This oil is heated to 90° C. and treated with 6.5 ml of chloroacetylchloride. After 2 h the mixture is diluted with 60 ml of 2-propanol, cooled to about 20° C. and seeded. The precipitated suspension is cooled to 0° C. The crystals are isolated by filtration, washed with cold 2-propanol and dried to obtain N-(2',6'-dichloro-4'-methylphenyl)-N-chloroacetyl-4-methylaniline. Mp: 140-141° C.

$^1$H-NMR (DMF-d7, 413K, 400 Mz) 2.33 (s, 3H, CH$_3$); 2.40 (s, 3H, CH$_3$); 4.18 (s, 2H, CH$_2$); 7.22 [d, 2H, HC (5) and HC (3)]; 7.38 [d, 2H, HC (2) and HC (6)]; 7.42 [s, 2H, HC (3') and HC (5')].

Example 6b)

N-(2'-chloro-6'-fluorophenyl)-N-chloroacetyl-4-methylaniline

Same procedure as example 6a, starting from 2-chloro-6-fluorophenol

Mp: 80-82° C.

$^1$H-NMR (DMF-d7, 393K, 400 Mz) 2.4 (s, 3H, CH$_3$); 4.3 (s, 2H, CH$_2$); 7.35 [d, 2H, HC (3) and HC (5)]; 7.43 [ddd, 1H, HC (5')]; 7.48 [d, 2H, HC (2) and HC (6)]; 7.55 [d, 1H, HC (3')]; 7.6 [ddd, 1H, HC (4')].

Example 6c)

N-(2',3',6'-trifluorophenyl)-N-chloroacetyl-4-ethylaniline

Same procedure as example 6a, starting from 2,3,6-trifluorophenol and 2-chloro-N-(4-ethylphenyl)acetamide. The crude intermediate N-(2',3',6'-trifluorophenyl)-4-ethylaniline was roughly purified by filtration on silica using toluene as eluent.

Mp: 49-50° C. $^1$H-NMR (DMF-d7, 413K, 400 MHz) 1.24 (t, 3H, CH$_3$); 2.70 (q, 2H, CH$_2$—CH$_3$); 4.25 (s, 2H, CH$_2$—Cl); 7.20 [m, 1H, HC (5')]; 7.34 [d, 2H, HC (3) and HC (5)]; 7.42 [d, 2H, HC (2) and HC (6)]; 7.46 [m, 1H, HC (4')].

Example 6d)

N-(2'-chloro-6'-fluorophenyl)-N-chloroacetyl-4-ethylaniline

Same procedure as example 6a starting from 2-chloro-6-fluorophenol and 2-chloro-N-(4-ethylphenyl)acetamide.

Mp: 67-68° C. $^1$H-NMR (DMF-d7, 413K, 500 MHz) 1.23 (t, 3H, CH$_3$); 2.68 (q, 2H, CH$_2$—CH$_3$); 4.20 (s, 2H, CH$_2$—Cl); 7.29 [d, 2H, HC (3) and HC (5)]; 7.34 [m, 1H, HC (5')]; 7.43 [d, 2H, HC (2) and HC (6)]; 7.48 [m, 2H, HC (3') and HC (4')].

Example 6e)

N-(2',6'-dichlorophenyl)-N-chloroacetyl-4-methylaniline

Same procedure as example 6a starting from 2,6-dichlorophenol and 2-chloro-N-(4-methylphenyl)acetamide. At the end of the acetylation reaction the mixture was diluted with a small amount of toluene (0.2 part) to prevent solidification.

Mp: 129-130° C. $^1$H-NMR (DMF-d7, 393K, 500 Mz) 2.40 (s, 3H, CH$_3$); 4.28 (s, 2H, CH$_2$—Cl); 7.30 [d, 2H, HC (3) and HC (5)]; 7.46 [d, 2H, HC (2) and HC (6)]; 7.54 [m, 1H, HC (4')]; 7.67 [d, 2H, HC (3') and HC (5')].

Compounds of Formula VII are cyclised to give lactams of Formula II

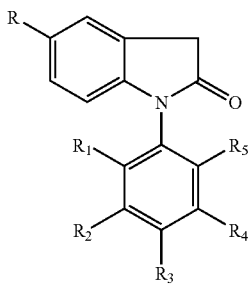

as described in Example 7

Example 7a)

N-(2',6'-dichloro-4'-methylphenyl)-5-methyloxindole

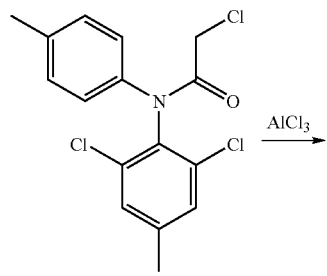

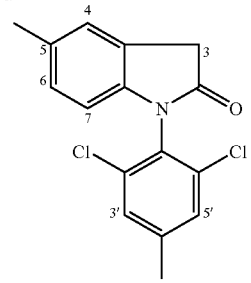

A mixture of 6.85 g (20 mmol) of N-(2',6'-dichloro-4'-methylphenyl)-N-chloroacetyl-4-methylaniline and 3.36 g (26 mmol) of aluminium chloride was heated slowly to 160-170° C. and held at this temperature for 3-4 h. During this time, nitrogen was continuously bubbled into the melt. The mixture was diluted with 20 ml of toluene and added on 20 ml of warm water. The organic layer was separated, washed with water and evaporated. The residue was crystallised from 20 ml of 2-propanol giving N-(2',6'-dichloro-4'-methylphenyl)-5-methyloxindole. Mp: 153-154° C.

$^1$H-NMR (DMSO-d6, 500 Mz, 300K) 2.29 [s, 3H, CH$_3$—C (5)]; 2.41 [s, 3H, CH$_3$—C (4')]; 3.81 (s, 2H, CH$_2$); 6.27 [d, 1H, HC (7)]; 7.00 [d, 1H, HC (6)]; 7.19 [s, 1H, HC (4)]; 7.58 [s, 2H, HC (3') and HC (5')].

Example 7b)

N-(2'-chloro-6'-fluorophenyl)-5-methyloxindole

Same procedure as example 7a

Mp: 137-138° C. $^1$H-NMR (DMSO-d6, 500 MHz, 300K) 2.27 (s, 3H, CH$_3$); 3.83 (s, 2H, CH$_2$) 6.35 [d, 1H, HC (7)]; 7.01 [d, 1H, HC (6)]; 7.19 [s, 1H, HC (4)]; 7.52 [d, 1H, HC (5')]; 7.60 [d, 1H, HC (3')], 7.63 [d, 1H, HC (4')].

Example 7c)

N-(2',3',6'-trifluorophenyl)-5-ethyloxindole

Same procedure as example 7a. After 4 h reaction, 10% more aluminium chloride was added. Overall reaction time: 6 h.

Mp: 171-172° C. $^1$H-NMR (DMSO-d6, 500 Mz, 300K) 1.18 (t, 3H, CH$_3$); 2.60 [q, 2H, CH$_2$—CH3]; 3.89 [s, 2H, CH$_2$—CO]; 6.62 [d, 1H, HC (7)]; 7.09 [d, 1H, HC (6)]; 7.25 [s, 1H, HC (4)]; 7.46 [m, 1H, HC (5')]; 7.76 [m, 1H, HC (4')].

Example 7d)

N-(2'-chloro-6'-fluorophenyl)-5-ethyloxindole

Same procedure as example 7c.

Mp: 129-130° C. $^1$H-NMR (DMSO-d6, 300K, 500 Mz) 1.18 (t, 3H, CH$_3$); 2.59 [q, 2H, CH$_2$—CH$_3$]; 3.86 (s, 2H, CH2-CO); 6.39 [d, 1H, HC (7)]; 7.05 [d, 1H, HC (6)]; 7.24 [s, 1H, HC (4)], 7.59 [m, 1H, HC (5')]; 7.64 [m, 2H, HC (3') and HC (4')].

Example 7e)

N-(2',6'-dichlorophenyl)-5-methyloxindole

Same procedure as 7a
$^1$H-NMR (DMSO-d6, 500 MHz, 300K) 2.30 (s, 3H, CH$_3$); 3.85 (s, 2H, CH$_2$); 6.29 [d, 1H, HC (7)]; 7.02 [d, 1H, HC (6)]; 7.22 [s, 1H, HC (4)], 7.62 [t, 1H, HC (4')]; 7.76 [d, 2H, HC (3') and HC (5')].

Example 7f)

N-(2',3',4',6'-Tetrafluorophenyl)-5-methyloxindole

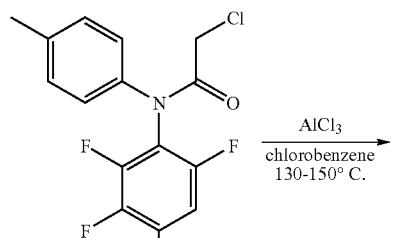

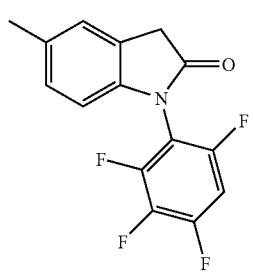

The solution of N-(2',3',4',6'-tetrafluorophenyl)-N-chloroacetyl-4-methylaniline (0.97 g, 2.97 mmol) in chlorobenzene (2.5 g) is treated with aluminum trichloride (1.05 g, 7.8 mmol) and the mixture is heated with stirring in an oil bath (155° C.) for 5 h while flushing the flask with nitrogen. Toluene (30 ml) and water (20 ml) are added and stirring is continued for 30 minutes at room temperature. The phases are separated and the organic phase is washed with hydrochloric acid (2N) and water. Evaporation under reduced pressure affords a solid (0.84 g, 2.85 mmol) which is recrystallised from 2-propanol to afford pure N-(2',3',4',6'-tetrafluorophenyl)-5-methyloxindole, mp. 172-173° C.

$^1$H-NMR (300 MHz, 300K, CDCl$_3$): 2.28 (s, 3H, CH$_3$); 3.65 [s, 2H, H$_2$C (3)]; 6.39 [d, 7.5 Hz, 1H, HC (7)]; 6.85-7.0 [m, 1H, HC (5')]; 6.98 üd, 7.5 Hz, 1H, HC (6)]; 7.09 [s, 1H, HC (4)].

Example 7 g)

N-(2'-Chloro-6'-methylphenyl)-5-ethyloxindole

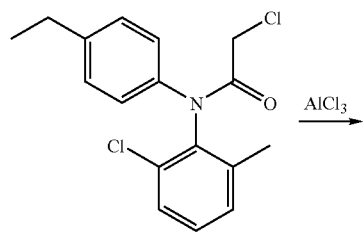

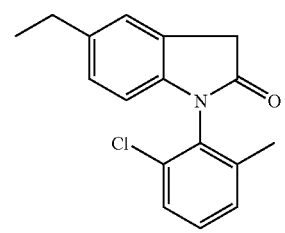

In a flask are mixed N-(2'-chloro-6'-methylphenyl)-N-chloroacetyl-4-ethylaniline (2.08 g) are mixed with aluminum trichloride (1.16 g) and the mixture is flushed with nitrogen. The flask is introduced into an oil bath (155-160° C.) and the mixture is stirred under a stream of nitrogen for 4.5 hours. The mixture is slightly cooled to about 100° C., treated with toluene (30 ml) and 1N HCl (20 ml) and stirred for 30 minutes while the temperature decreases gradually. After phase separation, the organic phase is washed with 1N HCl and water, dried (magnesium sulfate) and evaporated. The residue is chromatographed on silica (86 g) using toluene containing 5-20% isopropyl acetate as eluent affording the title product.

Mp: 125-126° C.

In a yet further alternative lactams of Formula II are prepared by oxidation of an unsaturated lactam of Formula III

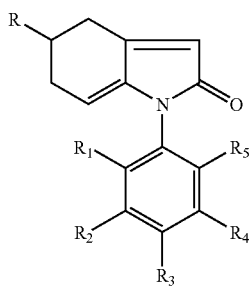

III which may be prepared, for instance as described in Example 8.

Example 8

(5-Ethyl-2-morpholin-4-yl-cyclohex-2-enylidene)-acetic acid ethyl ester

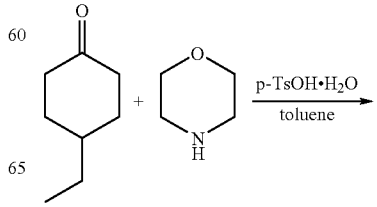

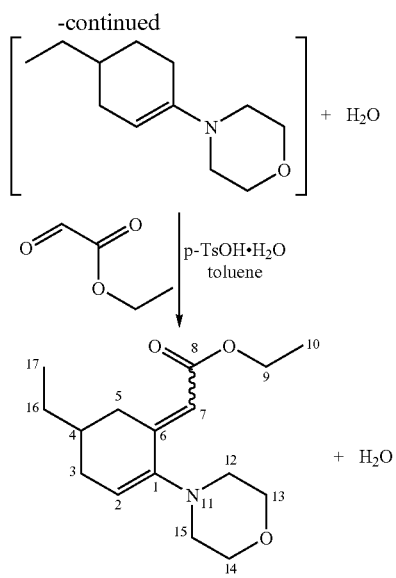

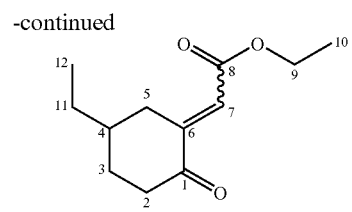

91.6 g of 4-Ethyl-cyclohexanone, 73.6 g of morpholine and 2 g of p-toluene-sulfonic acid monohydrate are dissolved in 400 ml of toluene. The mixture is heated to reflux and the water formed is removed by a water separator. After reacting for about 24 h, the reaction mixture is cooled to 100° C. and 2 g of p-toluene-sulfonic acid are added, followed by the addition of 157.22 g of glyoxylic acid ethyl ester during 30 minutes. The mixture is again heated to reflux for 5 hours and allowed to cool down to 22° C. The solvent is evaporated in vacuo and the crude product is distilled in vacuo at 140-150° C./$9.5^{-2}$ mbar.

$^1$H-NMR (CDCl$_3$, 500 MHz, 277K) δ 0.896 ppm (t, J=7 Hz, 3H, H$_3$C (17)), 1.277 (t, J=7 Hz, 3H, H$_3$C (10)), 1.20-1.45 (m, 2H, H$_2$C (16)), 1.50-1.62 (m, 1H, H—C (4)), 1.876 (ddd, J$_1$=18 Hz, J$_2$=9 Hz, J$_3$=3 Hz, 1H, H—C (3)), 2.13 (m, 1H, H—C (5)), 2.35 (dt, J$_1$=17 Hz, J$_2$=5 Hz, 1H, H—C (3)), 2.55-2.65 (m, 2H, H—C (12) and H—C (15)), 2.72-2.80 (m, 2H, H—C (12) and H—C (15)), 3.55 (dm, J=15 Hz, 1H, H—C (5)), 3.74 (m, 4H, H$_2$C (13) and H$_2$C (14)), 4.152 (q, J=7 Hz, 2H, H$_2$C (9)), 5.46 (dd, J$_1$=5 Hz, J$_2$=3 Hz, 1H, H—C (2)), 6.17 (broad s, 1H, H—C (7)). Assignments according to numbers given on the formula.

IR(film): strong absorptions at 2960, 1710, 1624, 1609, 1191, 1156 and 1120 cm$^{-1}$.

MS (EI): m/z 279 (M$^+$), 250 (M-C$_2$H$_5$)$^+$, 234, 206 (M-CO$_2$C$_2$H$_3$)$^+$, 176, 164, 135, 84.

b). Synthesis of (5-Ethyl-2-oxo-cyclohexylidene)-acetic acid ethyl ester

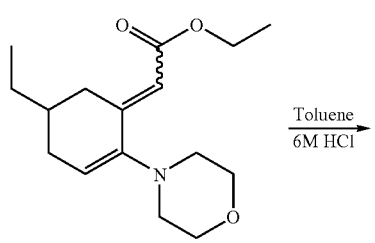

10 g of [5-Ethyl-2-morpholin-4-yl-cyclohex-2-enylidene]-acetic acid ethyl ester are dissolved in 20 ml of toluene. 12 ml of 6M HCl are added dropwise under rigorous stirring and the reaction mixture is stirred for additional 60 minutes at 22° C. The organic layer is separated and washed with 25 ml of water twice. The combined water layers are extracted with 25 ml of toluene. The combined toluene layers are dried over anhydrous sodium sulfate and the solvent is evaporated in vacuo to yield 6.72 g of [5-ethyl-2-oxo-cyclohexylidene]-acetic acid ethyl ester as an oil.

$^1$H-NMR (CDCl$_3$, 500 MHz, 277K) δ 0.935 ppm (t, J=7 Hz, 3H, H$_3$C (12)), 1.259 (t, J=7 Hz, 3H, H$_3$C (10)), 1.31-1.45 (m, 2H, H$_2$C (11)), 1.46-1.55 (m, 1H, H—C (5)), 1.59-1.69 (m, 1H, H—C (4)), 1.97-2.04 (m, 1H, H—C (5)), 2.296 (ddd, J=17 Hz, 11 Hz and 3 Hz, 1H, H—C (3)), 2.383 (m, 1H, H—C (6)), 2.615 (dt, J=17 and 4 Hz, 1H, H—C (6)), 3.57 (dm, J=17 Hz, 1H, H—C (3)), 4.17 (q, J=7 Hz, 2H, H$_2$C (9)), 6.42 (m, 1H, H—C (7)). Assignments according to numbers given on the formula.

IR(film): strong absorptions at 1719, 1698 and 1200 cm$^{-1}$.

MS (EI): m/z 210 (M$^+$), 164 (M-C$_2$H$_5$OH)$^+$, 135.

c). Synthesis of 1-(2-Chloro-6-methyl-phenyl)-5-ethyl-1,4,5,6-tetrahydro-indol-2-one

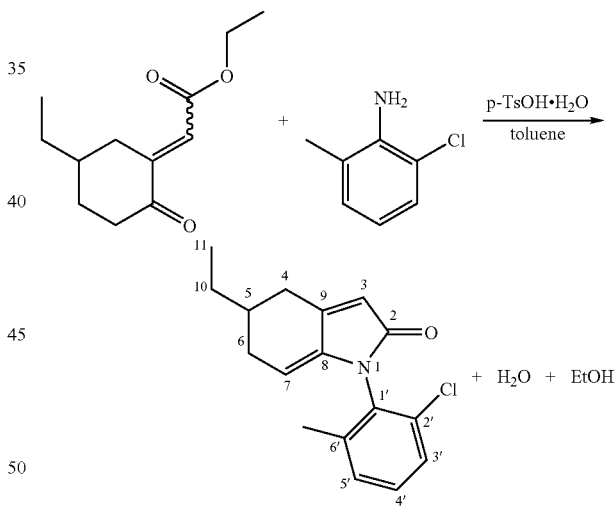

3.45 g of 2-Chloro-6-methyl-aniline are dissolved in 26 ml of toluene. 0.227 g of p-toluene-sulfonic acid (mono hydrate) are added and the mixture is heated to reflux. A solution of 5.0 g of (5-Ethyl-2-oxo-cyclohexylidene)-acetic acid ethyl ester in 13 ml of toluene is added drop-wise during 75 minutes and the water formed is collected by the means of a water separator. The reaction mixture is heated to reflux for 15 hours, during which time the condensing solvent is frequently removed and replaced by fresh toluene. For work-up, the mixture is cooled to 22° C. and is treated with 70 ml of saturated aqueous sodium bicarbonate solution under rigorous stirring. The layers are separated and the toluene phase is washed with a 5% aqueous solution of citric acid and finally with a 10% solution of sodium chloride in water. The aqueous phases are extracted with 70 ml of toluene and the toluene phases are combined. The solvent is evaporated in vacuo to yield 7.1 g of the crude product as a highly viscous oil. An analytical sample of the crude product can be purified by chromatography on silica gel using toluene/ethyl acetate (9:1) as eluent to yield pure 1-(2-Chloro-6-methyl-phenyl)-5-ethyl-1,4,5,6-tetrahydro-indol-2-one.

¹H-NMR (d₆-DMSO, 400 MHz, 300K) δ 0.894 ppm (t, J=7 Hz, 3H, H₃C (11)), 1.34-1.43 (m, 2H, H₂C (10)), 1.70-1.82 (m, 1H, H—C (5)), 1.90-2.02 (m, 1H, H—C (6)), 2.038 (s, 3H, H₃C (6')), 2.28-2.40 (m, 2H, H—C (4) and H—C (6)), 2.87 (dd, J₁=17 Hz and J₂=4 Hz, 1H, H—C (4)), 5.14 (m, 1H, H—C (7)), 5.96 (broad s, 1H, H—C (3)), 7.3-7.5 (m, 3H, H—C (3'), H—C (4'), H—C (5'). Assignments according to the numbers given on the formula.

IR (film): strong absorptions at 1703, 1660 and 1476 cm⁻¹.

MS (EI): m/z 287 (M⁺), 272 (M-CH₃) 258 (M-C₂H₅)⁺, 252 (M-Cl)⁺.

d): Synthesis of N-(2-Chloro-6-methyl-phenyl)-5-ethyl-oxindole

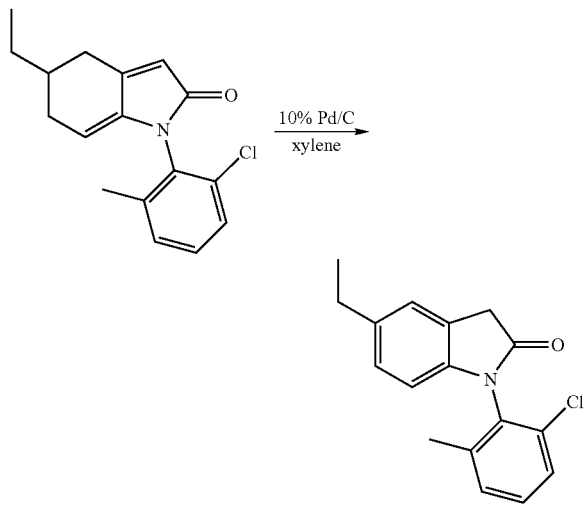

1-(2-Chloro-6-methyl-phenyl)-5-ethyl-1,4,5,6-tetrahydro-indol-2-one can be oxidized by classical methods, e.g. with 10% Pd—C in refluxing xylene to yield N-(2-Chloro-6-methyl-phenyl)-5-ethyl-oxindole.

¹H-NMR and MS spectra see example 7g.

Lactams of Formula II as defined above are converted to compounds of Formula I as defined above, for instance as described in Example 9 below.

Example 9a)

5-Methyl-2-(2',6'-dichloro-4'-methylanilino)phenylacetic acid

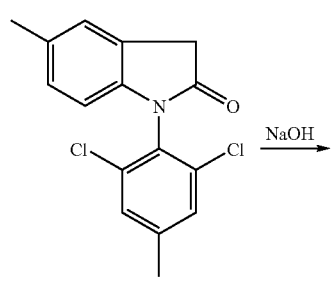

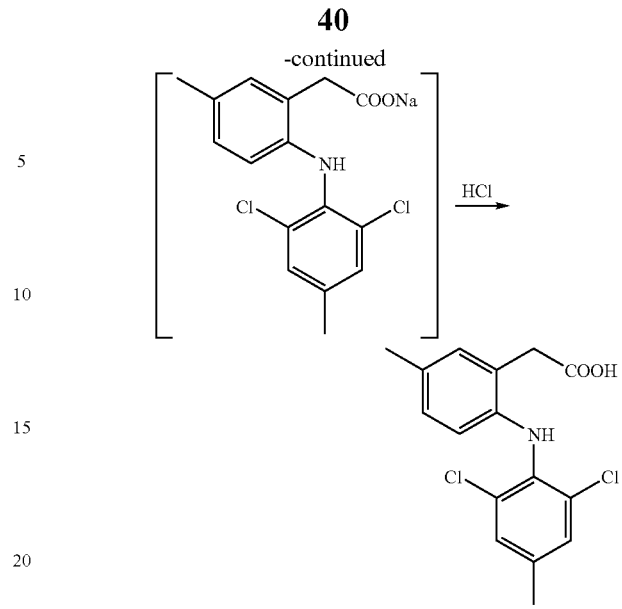

A mixture of 1.5 g of N-(2',6'-dichloro-4'-methylphenyl)-5-methyloxindole, 18 ml of ethanol and 1 ml of water is heated to reflux. 1.9 g of a 30% sodium hydroxide solution is slowly added and reflux is continued for 4-5 h. The solution is cooled to about 40° C. and treated slowly with a solution of 1.5 g of concentrated hydrochloric acid in 12 ml of water up to a pH of 3-4. The obtained suspension is cooled to 20° C. The crystals are collected by filtration, washed with water and dried giving 5-Methyl-2-(2',6'-dichloro-4'-methylanilino)phenylacetic acid.

Mp: 179-182° C. ¹H-NMR (DMSO-d6, 300K, 500 Mz) 2.22 [s, 3H, CH₃—C (5)]; 2.32 [s, 3H, CH₃—C (4)]; 3.67 (s, 2H, CH₂); 6.18 [d, 1H, HC (3)], 6.87 [s, d, 1H, HC (4)]; 6.97 (s, 1H, NH); 7.02 [s, 1H, HC (6)]; 7.36 [s, 2H, HC (3') and HC (5')]; 12.68 (br.s, 1H, COOH).

Example 9b)

5-Methyl-2-(2'-chloro-6'-fluoroanilino)phenylacetic acid

Same procedure as 9a.

Mp: 152-154° C. ¹H-NMR (DMSO-d6, 500 MHz, 300K) δ 2.21 (s, 3H, CH₃), 3.64 (s, 2H, CH₂); 6.42 [dd, 1H, HC (3)], 6.90 [dd, 1H, HC (4)], 7.01 [d, 1H, HC (6)], 7.09 (s, 1H, NH), 7.09 [ddd, 1H, HC (4')], 7.23 [ddd, 1H, HC (5')], 7.34 [ddd, 1H, HC (3')], 12.67 (s, 1H, COOH).

Example 9c)

5-Methyl-2-(2',3',4',6'-tetrafluoroanilino)-phenylacetic acid

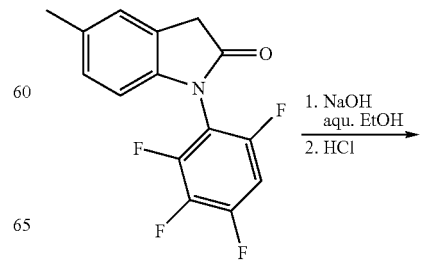

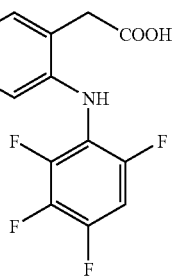

The suspension of 350 mg of N-(2′,3′,4′,6′-tetrafluorophenyl)-5-methyloxindole in 20 ml of ethanol and 5 ml of water is degassed by passing through nitrogen for 1.5 h. Then 260 mg of 30% aqueous sodium hydroxide is added and the mixture is heated to reflux for 6.5 hours. Most of the ethanol is then removed by distillation the mixture is cooled to room temperature followed by the slow addition of 1N hydrochloric acid (1.05 g) to reach a pH of about 3. The precipitate is then filtered, washed with ethanol/water (1:1) and dried in vacuo at room temperature affording the title product.

Mp: 145-146° C.

$^1$H-NMR (300 MHz, DMSO-d6): 2.23 (s, 3H, CH3); 3.65 (s, 2H, CH2-COO); 6.55 [s, 1H, HC (3)]; 6.92 [d, 1H, HC (4)]; 7.00 [s, 1H, HC86)]; 7.20 (s, 1H, NH); 7.50 [m, 1H, HC (5′)].

Similarly other lactams of formula II are converted to compounds of Formula I substantially as described above.

The invention claimed is:

1. A process for the production of a compound of Formula I or a pharmaceutically acceptable salt thereof,

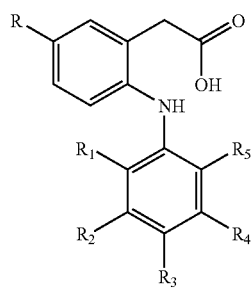

wherein R is methyl or ethyl;
$R_1$ is chloro or fluoro;
$R_2$ is hydrogen or fluoro;
$R_3$ is hydrogen, fluoro, chloro, methyl, ethyl, methoxy, ethoxy or hydroxy;
$R_4$ is hydrogen or fluoro; and
$R_5$ is chloro, fluoro, trifluoromethyl or methyl,
provided that $R_1$, $R_2$, $R_4$ and $R_5$ are not all fluoro when R is ethyl and $R_3$ is H; comprising:
a) rearrangement and hydrolysis of a compound of formula IX

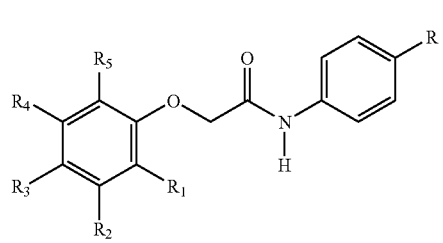

to produce a compound of formula VIII;

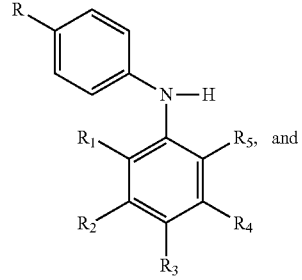

b) transforming the compound of formula VIII into the compound of formula I.

2. A process according to claim 1 for the production of a compound of Formula I, or a pharmaceutically acceptable salt thereof,

I wherein
R is methyl or ethyl;
$R_1$ is chloro or fluoro;
$R_2$ is hydrogen or fluoro;
$R_3$ is hydrogen, fluoro, chloro, methyl, ethyl, methoxy, ethoxy or hydroxy;
$R_4$ is hydrogen or fluoro; and
$R_5$ is chloro, fluoro, trifluoromethyl or methyl,
provided that $R_1$, $R_2$, $R_4$ and $R_5$ are not all fluoro when R is ethyl and $R_3$ is H; comprising the steps of:
(a) rearrangement and hydrolysis of a compound of formula IX

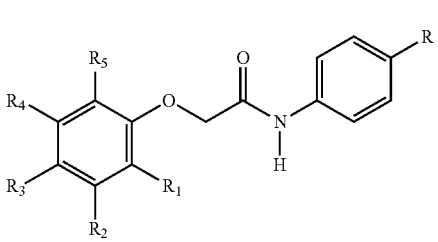

to produce a compound of formula VIII

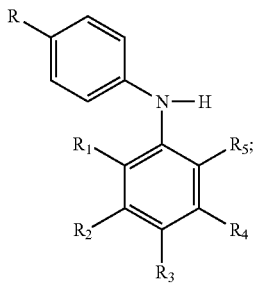

(b) N-acylation of the compound of formula VIII with a haloacetyl chloride to produce a compound of formula VII

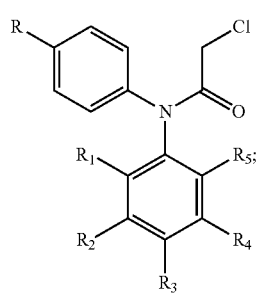

(c) cyclisation of the compound of formula VII to produce a lactam of formula II

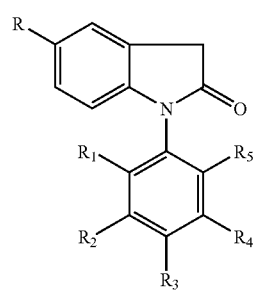

and
(d) cleaving the lactam with a base.

3. The process according to claim 1, wherein the compound of formula IX is produced by alkylation of a compound of formula XII

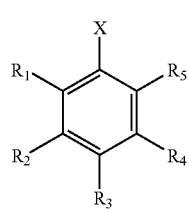

with 2-chloro-N-(4-methylphenyl)acetamide or 2-chloro-N-(4-ethylphenyl)acetamide.

4. The process according to claim 1 for the preparation of a compound selected from the group consisting of:
5-methyl-2-(2',4'-dichloro-6'-methylanilino)phenylacetic acid;
5-methyl-2-(2', 3', 5', 6'-tetrafluoroanilino)phenylacetic acid;
5-methyl-2-(2', 3', 4', 6'-tetrafluoroanilino)phenylacetic acid;
5-methyl-2-(2',6'-dichloroanilino)phenylacetic acid;
5-methyl-2-(2',6'-dichloroanilino)phenylacetic acid, potassium salt;
5-methyl-2-(2',6'-dichloroanilino)phenylacetic acid, sodium salt;
5-methyl-2-(2'-chloro-6'fluoroanilino)phenylacetic acid;
5-methyl-2-(2',6'-dichloro-4'-methylanilino)phenylacetic acid;
5-methyl-2-(2'-chloro-6'-methylanilino)phenylacetic acid;
5-methyl-2-(2',4'-difluoro-6'-chloroanilino)phenylacetic acid;
5-methyl-2-(2'-fluoro-4',6'-dichloroanilino)phenylacetic acid;
5-methyl-2-(2'-chloro-4'-fluoro-6'-methylanilino)phenylacetic acid;
5-ethyl-2-(2'-fluoro-6'-chloroanilino)phenylacetic acid;
5-ethyl-2-(2'-chloro-6'-methylanilino)phenylacetic acid;
5-ethyl-2-(2',3',6'-trifluoroanilino)phenylacetic acid;
5-ethyl-2-(2',3',5',6'-tetrafluoro-4'-ethoxyanilino)phenylacetic acid;
5-ethyl-2-(2'-chloro-4',6'-difluoroanilino)phenylacetic acid;
5-ethyl-2-(2',4'-dichloro-6'-fluoroanilino)phenylacetic acid;
5-ethyl-2-(2',4'-dichloro-6'-methylanilino)phenylacetic acid;
5-ethyl-2-(2'-fluoro-4'-chloro-6'-methylanilino)phenylacetic acid;
5-ethyl-2-(2',4'-difluoro-6'-methylanilino)phenylacetic acid;
5-ethyl-2-(2'-chloro-4'-fluoro-6'-methylanilino)phenylacetic acid;
5-methyl-2-(2'-chloro-4'-hydroxy-6'-fluoroanilino)phenylacetic acid;
5-methyl-2-(2'-fluoro-6'-trifluoromethylanilino)phenylacetic acid;
5-methyl-2-(2',4'-dichloro-6'-trifluoromethylanilino)phenylacetic acid;
5-methyl-2-(2', 3', 4', 6'-tetrafluoroanilino)phenylacetic acid;
5-methyl-2-(2',6'-dichloroanilino)phenylacetic acid;
5-methyl-2-(2'-chloro-6'fluoroanilino)phenylacetic acid;
5-methyl-2-(2',6'-dichloro-4'-methylanilino)phenylacetic acid;
5-methyl-2-(2'-chloro-6'-methylanilino)phenylacetic acid;
5-methyl-2-(2'-chloro-4'-fluoro-6'-methylanilino)phenylacetic acid;
5-ethyl-2-(2'-fluoro-6'-chloroanilino)phenylacetic acid;
5-ethyl-2-(2'-chloro-6'-methylanilino)phenylacetic acid;
5-ethyl-2-(2',3',6'-trifluoroanilino)phenylacetic acid, and
5-ethyl-2-(2',4'-dichloro-6'-methylanilino)phenylacetic acid,
and pharmaceutically acceptable salts thereof.

5. The process according to claim 1, wherein:
R is methyl;
R1 is chloro;
R2, R3 and R4 are hydrogen and
R5 is fluoro.

* * * * *